(12) United States Patent
Frost et al.

(10) Patent No.: US 6,618,140 B2
(45) Date of Patent: Sep. 9, 2003

(54) SPECTRAL DECONVOLUTION OF FLUORESCENT MARKERS

(75) Inventors: Keith L. Frost, Seattle, WA (US); James K. Riley, Redmond, WA (US); David A. Basiji, Seattle, WA (US); William E. Ortyn, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 10/175,543

(22) Filed: Jun. 18, 2002

(65) Prior Publication Data

US 2003/0020908 A1 Jan. 30, 2003

Related U.S. Application Data

(60) Provisional application No. 60/299,164, filed on Jun. 18, 2001, and provisional application No. 60/306,126, filed on Jul. 17, 2001.

(51) Int. Cl.$^7$ .............................. G01J 3/30; G01N 21/64
(52) U.S. Cl. ................ 356/317; 250/458.1; 250/459.1; 250/461.2
(58) Field of Search ............................... 356/317, 318, 356/417; 250/458.1–461.2

(56) References Cited

U.S. PATENT DOCUMENTS

| | | | |
|---|---|---|---|
| 5,096,807 A | 3/1992 | Leaback | 435/6 |
| 5,929,986 A | 7/1999 | Slater et al. | 356/326 |
| 6,014,468 A | 1/2000 | McCarthy et al. | 382/254 |
| 6,210,973 B1 | 4/2001 | Pettit | 436/172 |

*Primary Examiner*—F. L. Evans
*Assistant Examiner*—Kara Geisel
(74) *Attorney, Agent, or Firm*—Ronald M. Anderson

(57) ABSTRACT

In an instrument generating images from the fluorescent emissions of a plurality of fluorescent dyes carried by objects in a flow stream, spectral dispersion is used to expand the images of the objects along one axis of a two-dimensional photosensor array according to emission wavelength. The dispersion is unable to completely separate the emissions of a plurality of dyes because the emission spectra of the dyes overlap in wavelength. The method of the present invention accomplishes accurate estimation of the intensity of the light received from each of a plurality of dyes by decomposing the two dimensional spectrally dispersed images into a set of characteristic parameters using either an iterative curve fitting optimization method or a linear algebraic method.

39 Claims, 17 Drawing Sheets

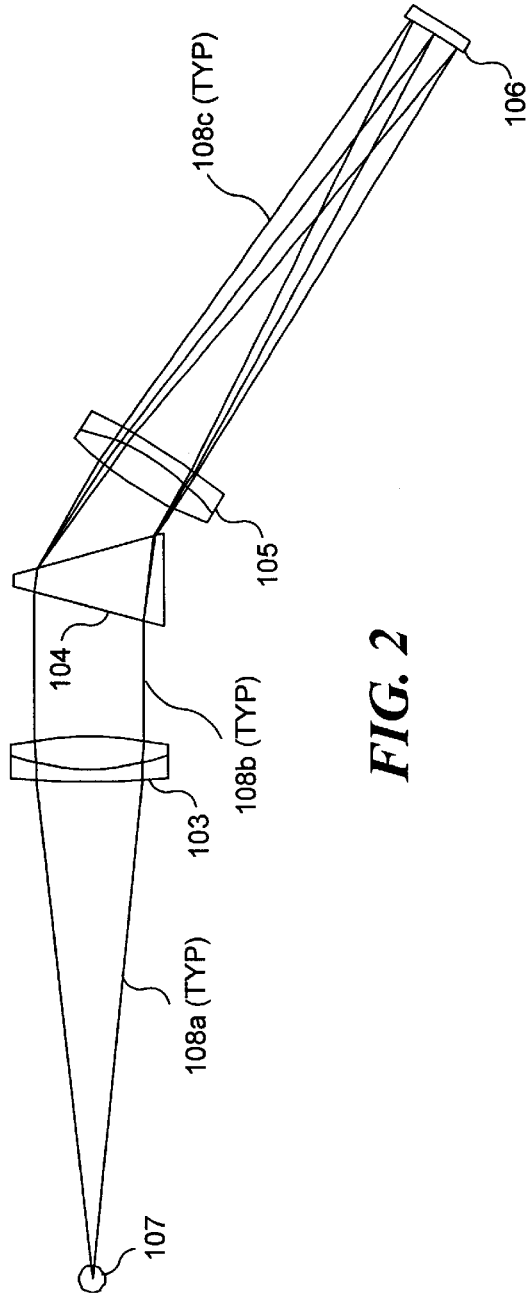
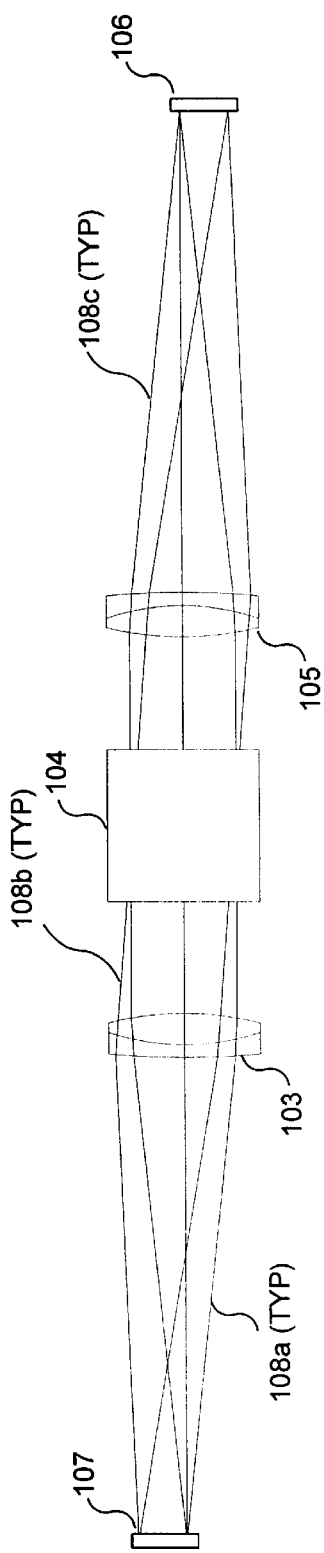
FIG. 2
FIG. 3

SPECTRAL DECONVOLUTION OF FLUORESCENT MARKERS

RELATED APPLICATIONS

This application is based on prior copending provisional applications Ser. No. 60/299,164, filed on Jun. 18, 2001, and Ser. No. 60/306,126, filed on Jul. 17, 2001, the benefits of the filing dates of which are hereby claimed under 35 U.S.C. § 119(e).

FIELD OF THE INVENTION

The present invention generally relates to a method and apparatus for accurately decomposing images constructed from the fluorescent emissions of a plurality of fluorescent dyes coexisting in a specimen, with application to a broad range of imaging instruments and particularly, to flow imaging instruments using time delay integration image detectors and spectral dispersion in a single plane accomplished using a prism.

BACKGROUND OF THE INVENTION

Fluorescent compounds are useful for labeling components of biological cells. Such labeling is useful for conducting basic research, as well as for medical diagnostic testing. Fluorescent compounds can facilitate the detection of molecular structures in cells. Cellular specimens are exposed to dyes in which molecules of one or more fluorophores are attached to molecules that bind with the target molecules in the cells. The binding mechanism may be an antigen-antibody interaction, or the hybridization of a target strand of nucleic acid with its complementary counterpart. In antigen-antibody interaction, the flourophore is attached to a protein complex. In the hybridization of a target strand, the fluorophore is attached to a strand of RNA or DNA of a particular base sequence.

Information about biological specimens stained with fluorescent markers can be collected by a variety of methods. Slides carrying cells or tissue sections may be viewed through a microscope equipped with the appropriate excitation sources and optical filters for the fluorophores in use. Alternatively, cells may be suspended in a liquid and passed through a flow cytometer equipped to detect and count cells displaying various bound fluorophores. A preferred flow imaging technology, utilizing time delay integration electronic image capture and computational image analysis to deliver information about the specimen, is disclosed in commonly assigned U.S. Pat. No. 6,211,955, the complete disclosure, specification, and drawings of which are hereby specifically incorporated by reference.

An extension of the technology of fluorescence flow imaging is that of utilizing multiple fluorescent dyes in a single specimen and separating the signals from the plurality of dyes by wavelength discrimination. While such multiplexed signals enable more information about each cell to be collected, the signal separation process can be challenging. It would be desirable to provide a signal separation process that accurately estimates the relative concentrations of fluorescent dyes bound to a specimen, and, therefore, about the relative abundances of a plurality of molecular species in the specimen. Such multiplexed information is especially valuable for characterizing the reactions of biological cells to compounds under investigation as potential therapeutic agents or for detecting abnormalities in genetic makeup or gene expression related to disease.

SUMMARY OF THE INVENTION

One aspect of the present invention is a method for processing an electrical signal containing data from at least two sources, to separate the electrical signal into components corresponding to each one of the at least two sources. Once the electrical signal containing data from at least two sources is obtained, it is processed to separate the electrical signal into portions corresponding to each one of the at least two sources. Once separated, amplitudes are derived for each portion of the electrical signal that corresponds one of the at least two different sources. Preferably each source is a fluorophore, and the amplitude for each fluorophore corresponds to a relative concentration for that fluorophore.

In one embodiment the electrical signal is processed using curve fitting to distinguish different portions of the electrical signal corresponding to different sources. The curve fitting can be achieved using Lorentzian equations.

A model of the spectra of the at least two sources is preferably obtained before processing the electrical signal. The step of using curve fitting to distinguish different portions of the electrical signal comprises the step of using nonlinear conjugation to reduce an error between the electrical signal and the model. More preferably, the step of using nonlinear conjugation is performed iteratively. In at least one embodiment, the error that is reduced by the nonlinear conjugation comprises a mean square error between the model and the electrical signal.

The electrical signal is preferably obtained by focusing light from an object including at least two sources along a collection path, and dispersing the light that is traveling along the collection path into a plurality of light beams, such that each light beam corresponds to a different wavelength. The plurality of light beams are focused to produce respective images for the light beams, and the images are directed to a detector, thereby generating the electrical signal.

In yet another embodiment, processing the electrical signal is achieved by solving a set of linear equations corresponding to an emission set defined by the at least two different sources.

Yet another aspect of the invention is directed to a method for determining a relative concentration of a specific fluorophore associated with an object that includes at least two different fluorophores. Light is focused from the object along a collection path. The light traveling along the collection path is dispersed into a plurality of light beams, such that each light beam corresponds to a different wavelength. A prism is preferably employed to achieve the dispersion. Each of the light beams is focused to produce a respective image, and the images are detected by a detector that produces an electric signal in response to the images. The electrical signal is processed to separate it into portions corresponding to each of the at least two different fluorophores. An amplitude is derived for each portion of the electrical signal that corresponds one of the at least two different fluorophores. The amplitude for each fluorophore corresponds to a relative concentration for that fluorophore.

The step of processing the electrical signal includes either using curve fitting to distinguish different portions of the electrical signal corresponding to different fluorophores from one another, or solving a set of linear equations based on an emission set defined by the different fluorophores represent in the electrical signal.

A model of the spectra of the at least two fluorophores is obtained before processing the electric signal, and the step of using curve fitting to distinguish different portions of the electrical signal includes the step of using nonlinear conjugation to reduce an error between the electrical signal and the model. Preferably, the nonlinear conjugation is performed iteratively. In at least one embodiment, the error that is reduced by the nonlinear conjugation comprises a mean square error between the model and the electrical signal.

In embodiments in which a set of linear equations is solved, the detector preferably comprises a scatter channel and a fluorescence channel. The step of solving a set of linear equations includes the steps of establishing a pixel positional reference for the scatter channel and the fluorescence channel of the detector, and determining a lateral shift in the fluorescence channel. The lateral shift is preferably determined with sub-pixel accuracy.

In addition to the aforementioned embodiments relating to the method, the present invention is also directed to a system having elements that carry out functions generally consistent with the steps of the method described above. Specifically, an imaging system is defined for determining a relative concentration of a specific fluorophore associated with an object. The imaging system includes a collection lens disposed so that light traveling from the object passes through the collection lens and travels along a collection path. A dispersing component is disposed in the collection path so as to receive the light that has passed through the collection lens, dispersing the light into a plurality of separate light beams. Each light beam is directed away from the dispersing component in a different predetermined direction. The system also includes an imaging lens disposed to receive the light beams from the dispersing component, thereby producing an ensemble of images that includes a plurality of images corresponding to each of the light beams. Each image is projected by the imaging lens toward a different predetermined location. A detector is disposed to receive the plurality of images produced by the imaging lens, and produces an output signal in response thereto. Finally, the system includes means for processing the output signal to separate the electrical signal into portions corresponding to different fluorophores, and to derive an amplitude for each portion of the electrical signal that corresponds to different fluorophores. The amplitude for each fluorophore corresponds to a relative concentration for that fluorophore.

The means for processing preferably includes a memory in which a plurality of machine instructions defining a signal conditioning software program are stored, and a processor that is coupled to the display, and to the memory to access the machine instructions. Execution of the machine instructions by the processor causes it to separate the electrical signal into portions corresponding to different fluorophores, and to derive an amplitude for each portion of the electrical signal that corresponds to a different fluorophore.

It is contemplated that the means for processing the signal might comprise either a programmed computer, an application specific integrated circuit (ASIC), or an oscilloscope.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 2 is a schematic plan view of the optical collection ray paths of the flow imaging system of FIG. 1, as viewed from above the plane of dispersion;

FIG. 3 is a schematic side elevational view of the optical collection ray, paths of the flow imaging system of FIG. 1, as viewed from an observation point in the plane of dispersion;

Figure 8:
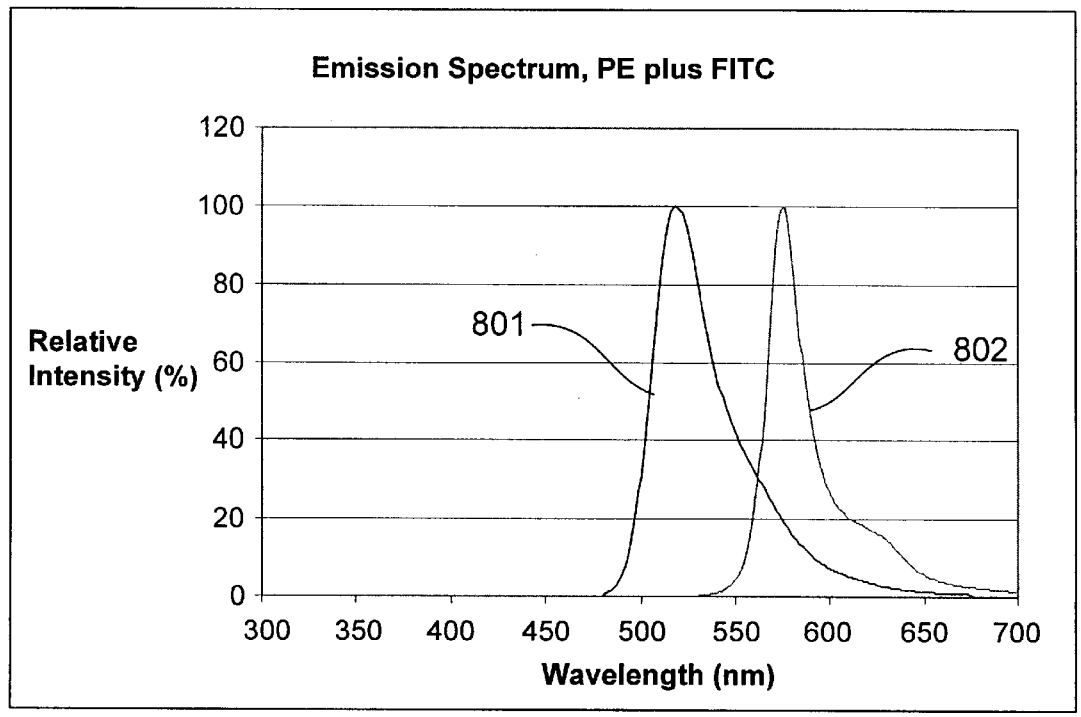
Figure 6:
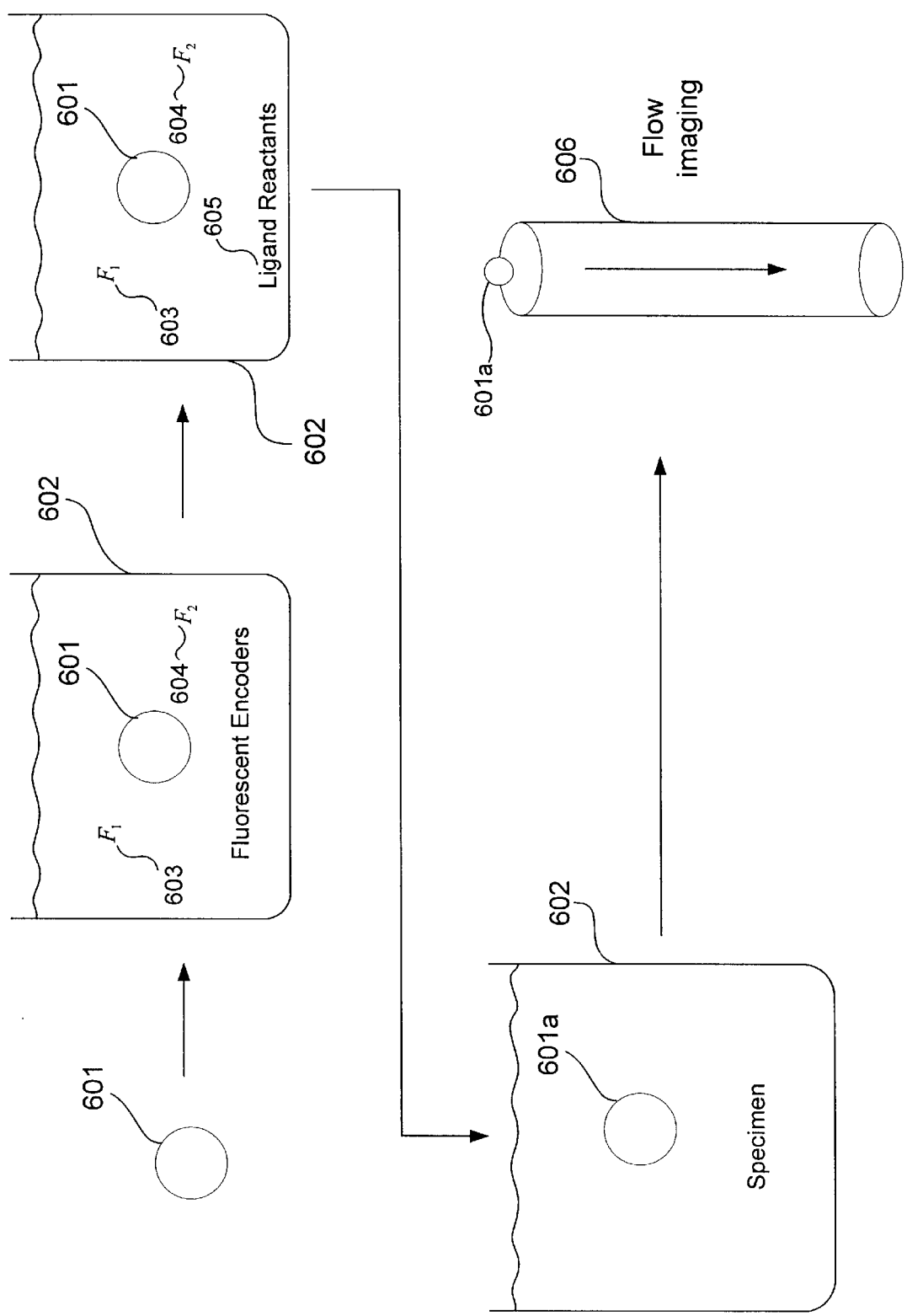
Figure 7:
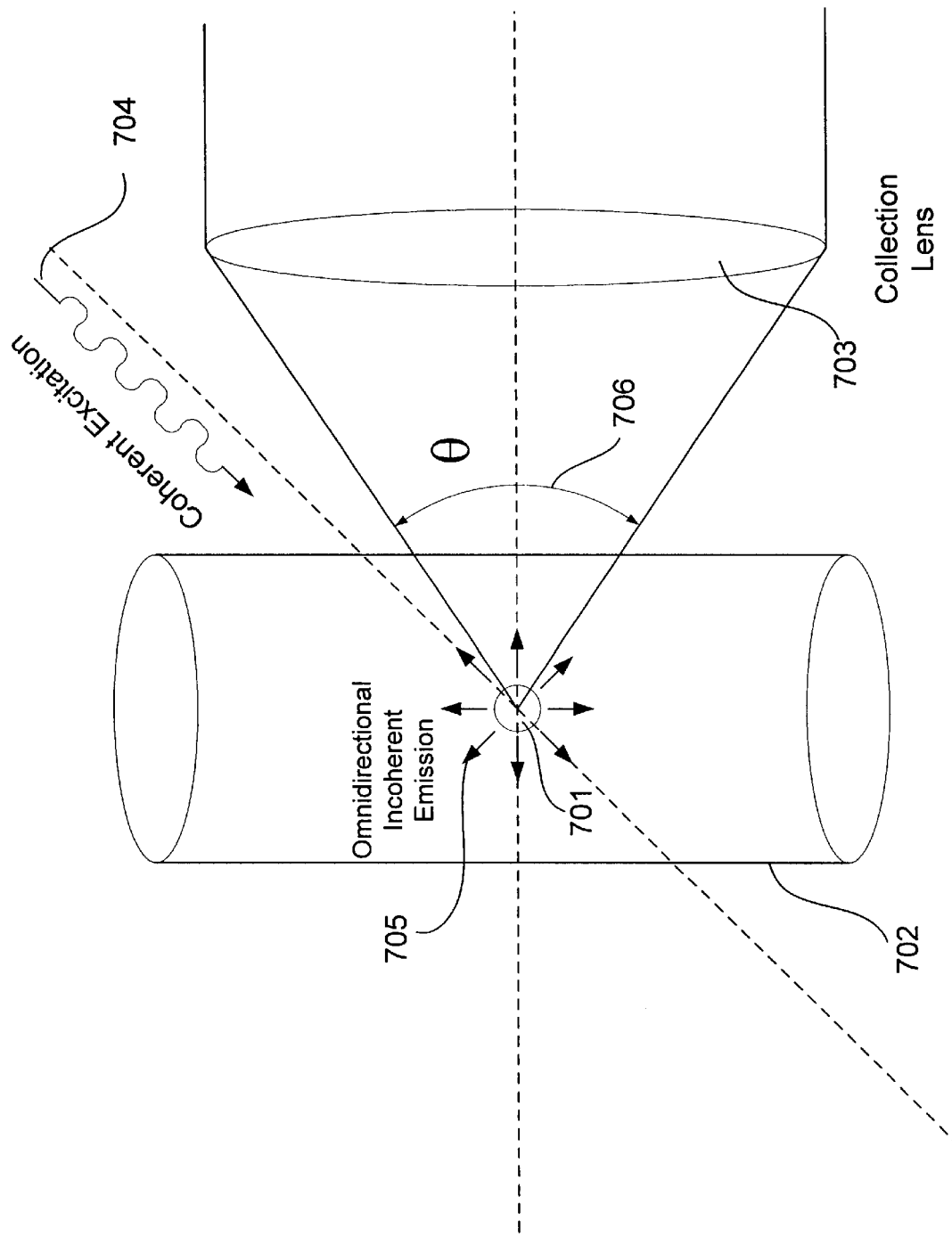
Figure 9:
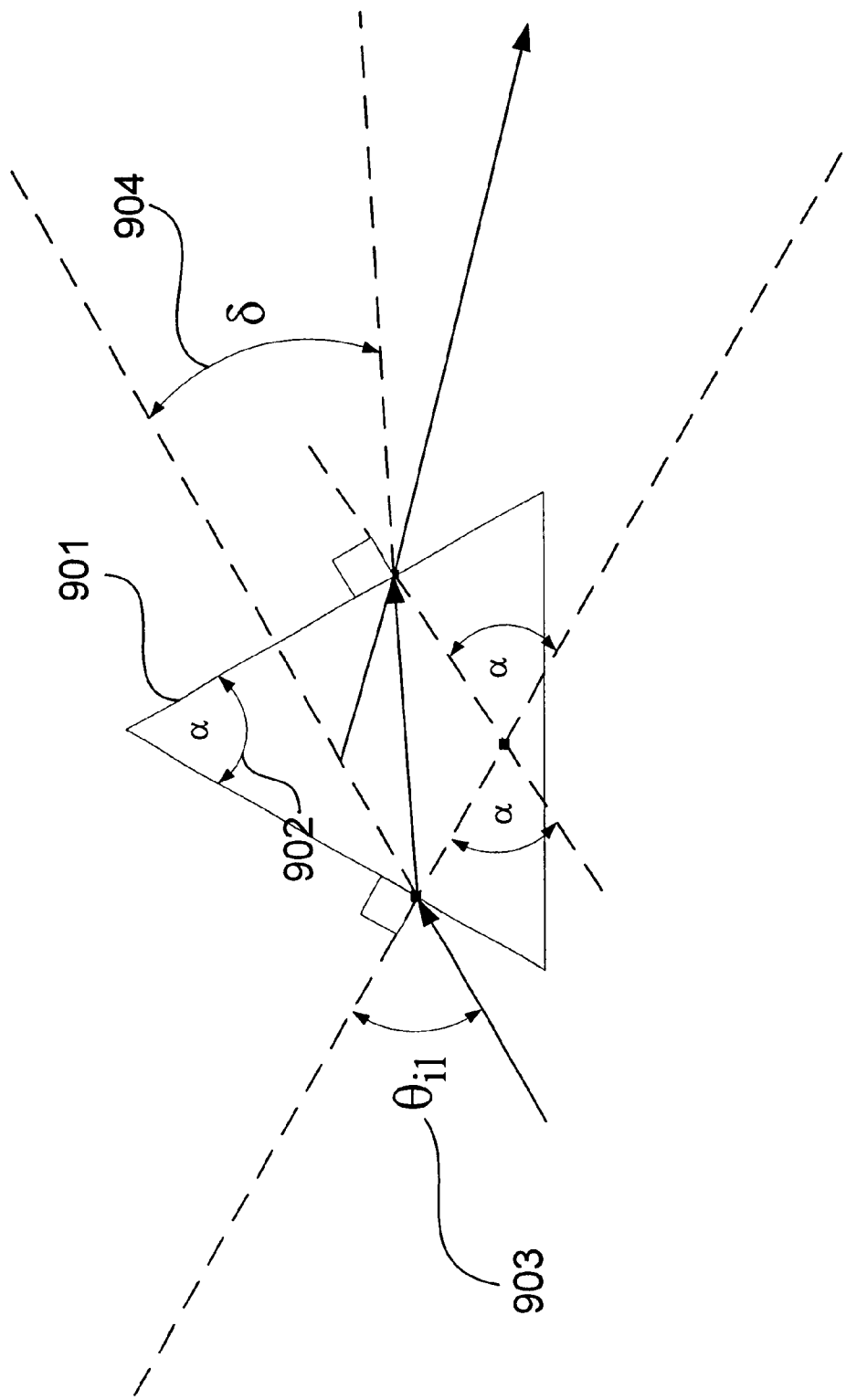
Figure 10:
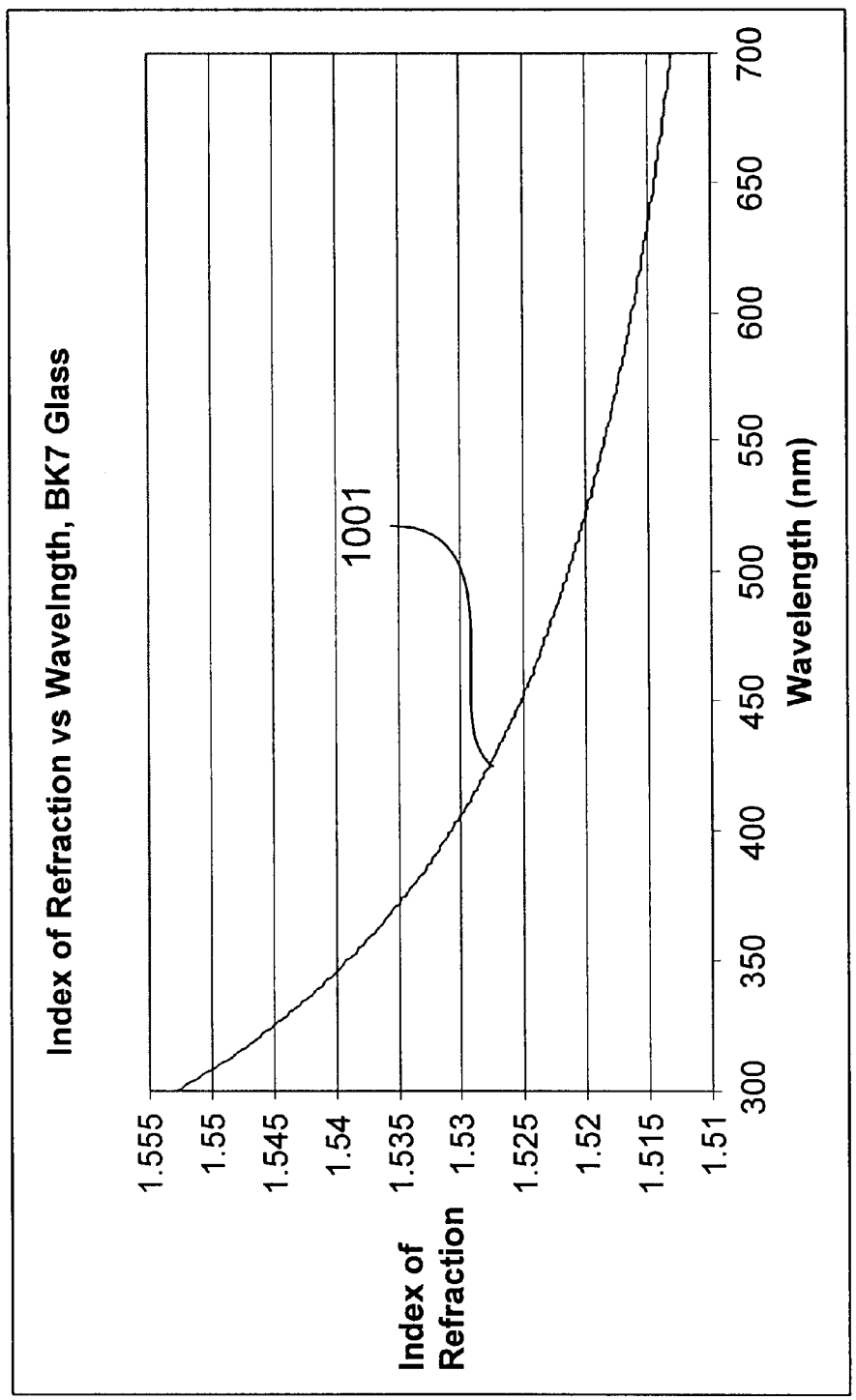
Figure 11:
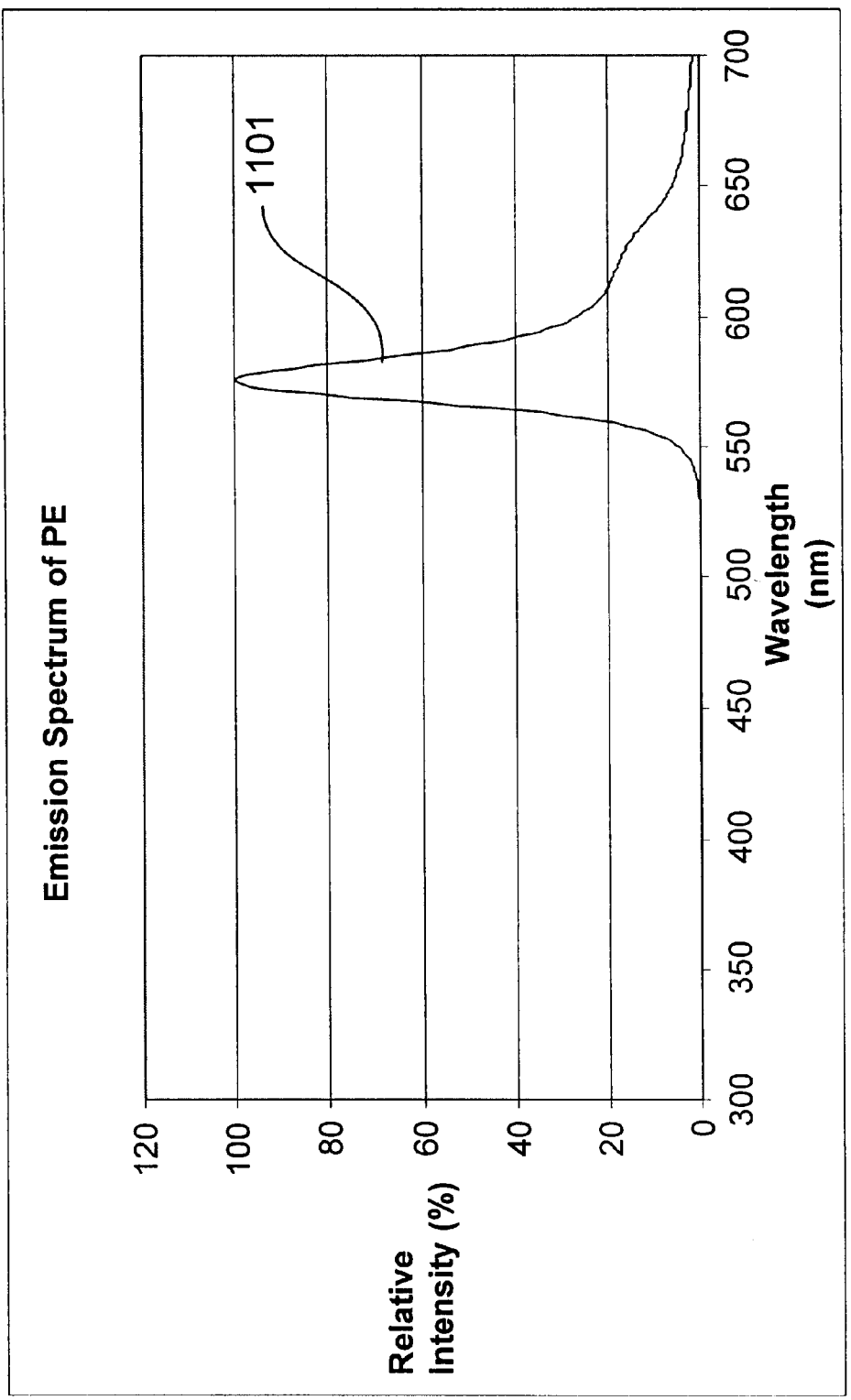
Figure 12:
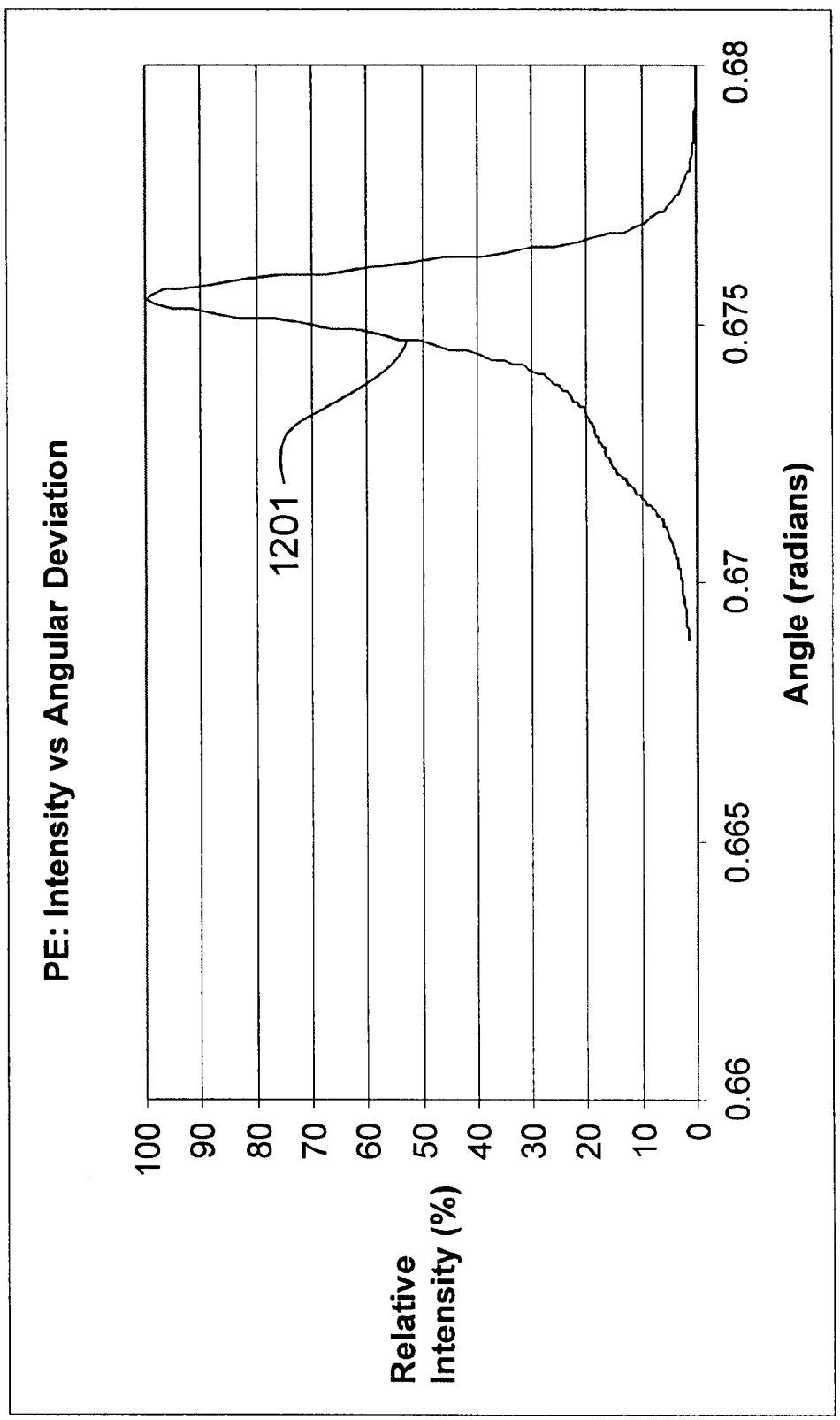
Figure 13:
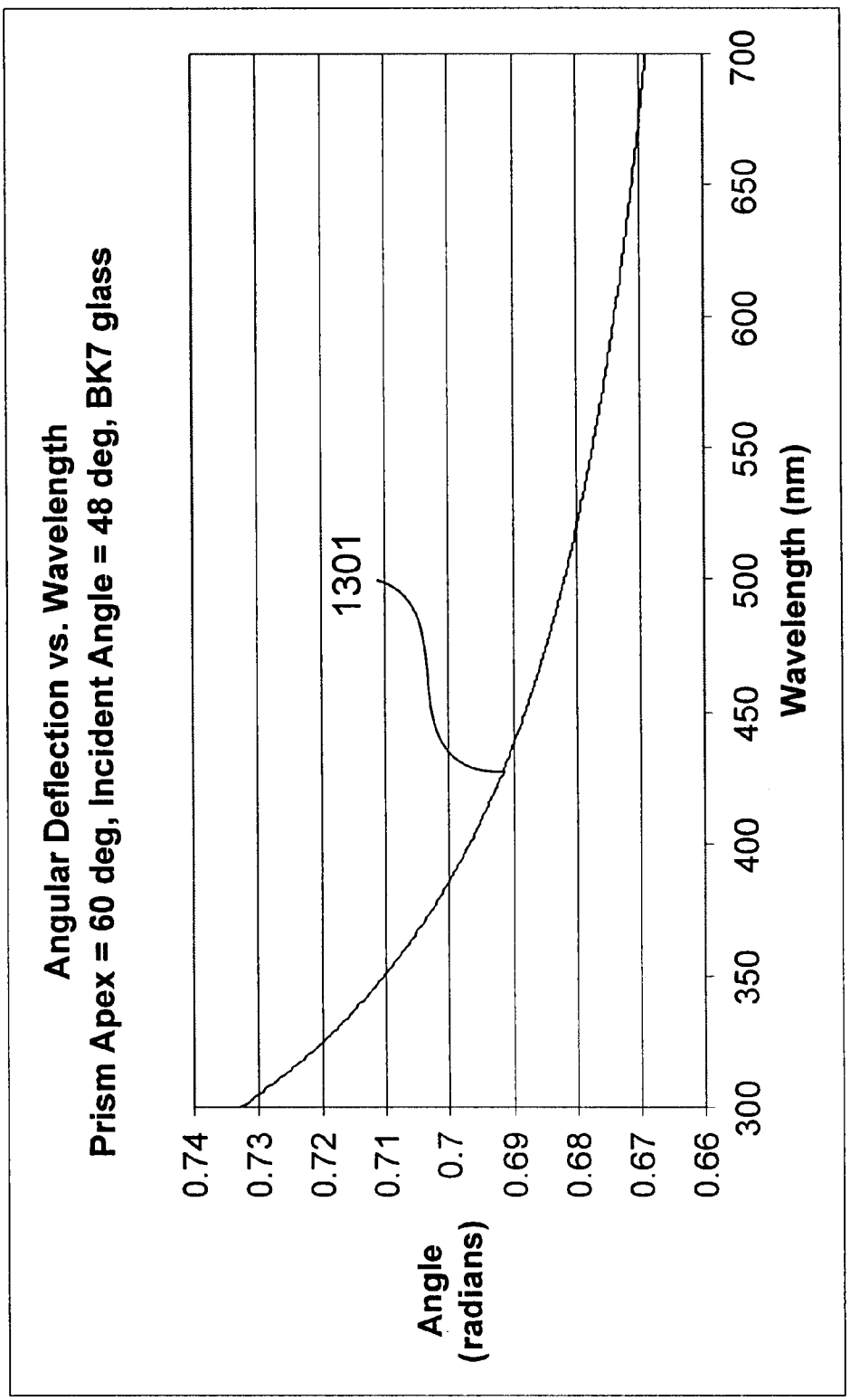
Figure 14:
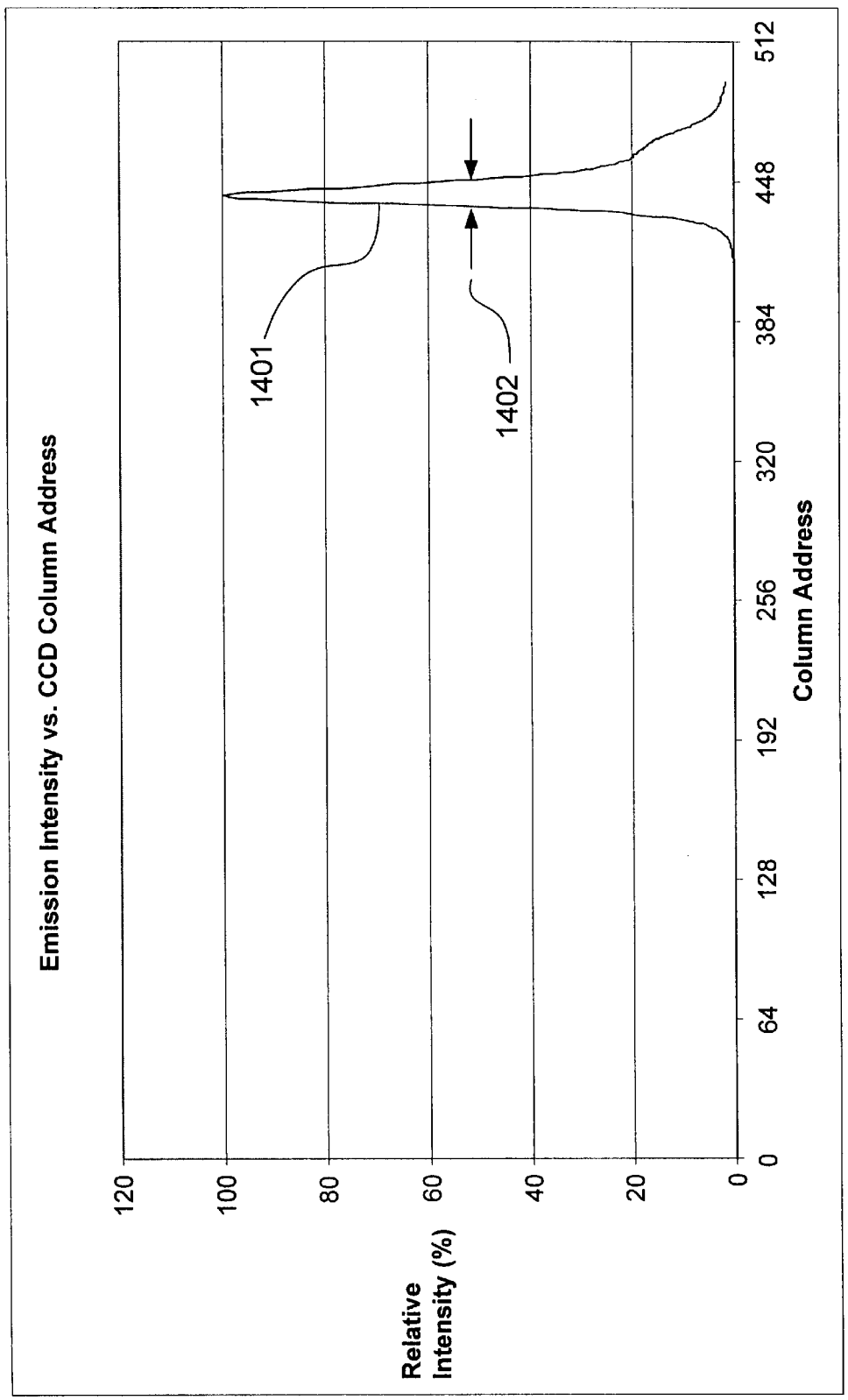
Figure 15:
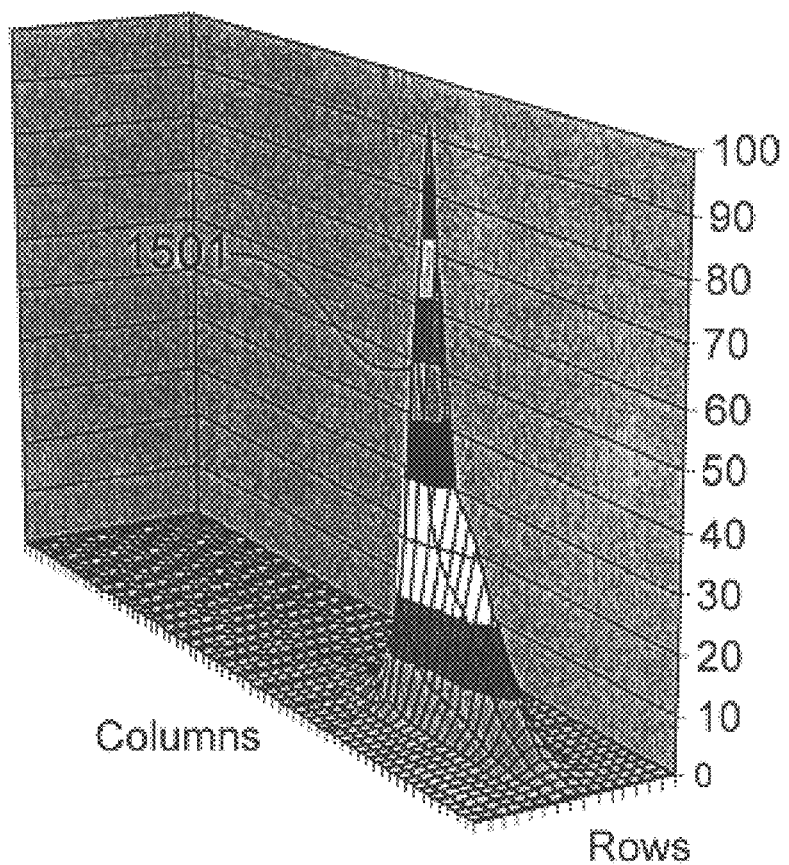
Figure 16:
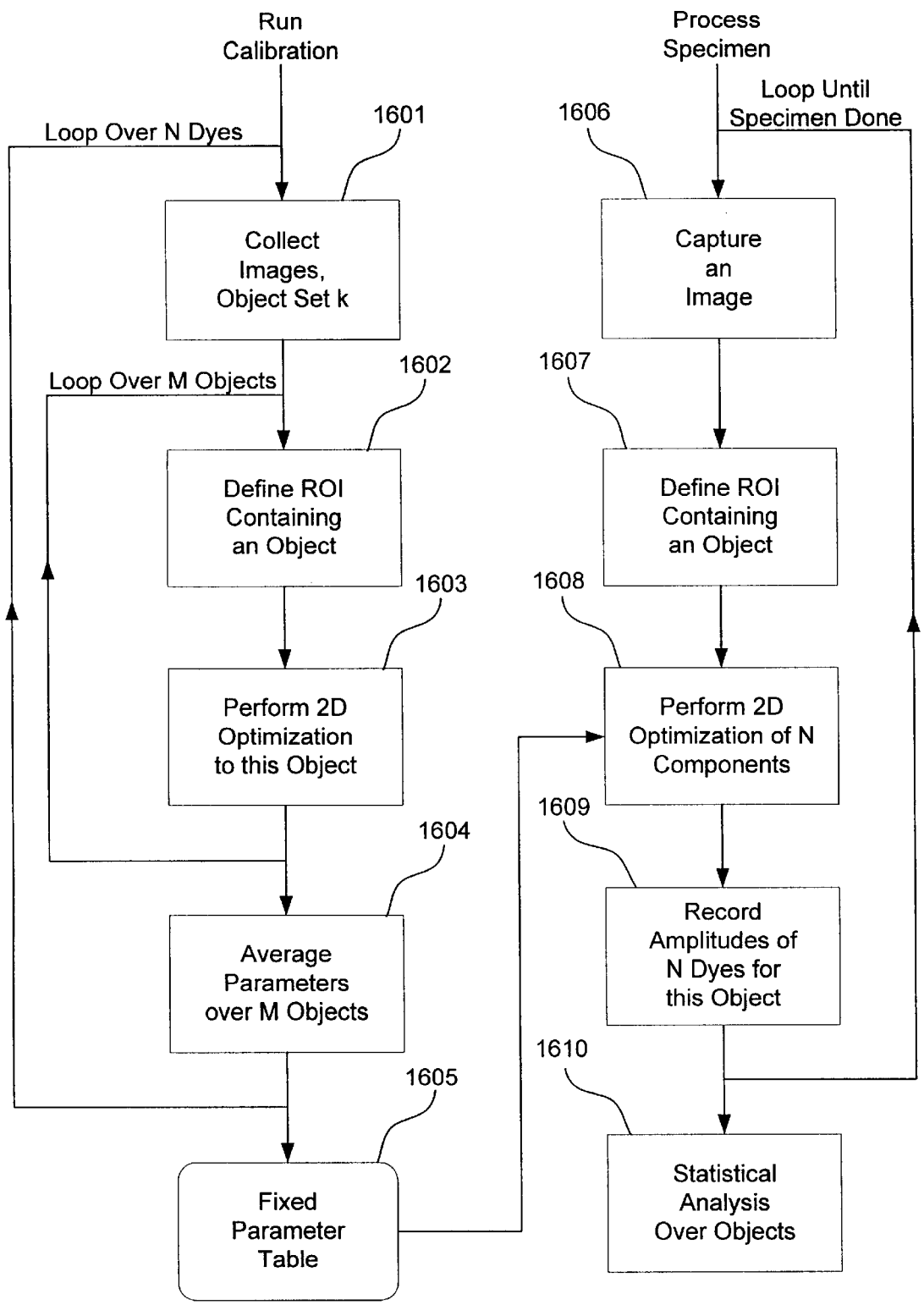
Figure 17:
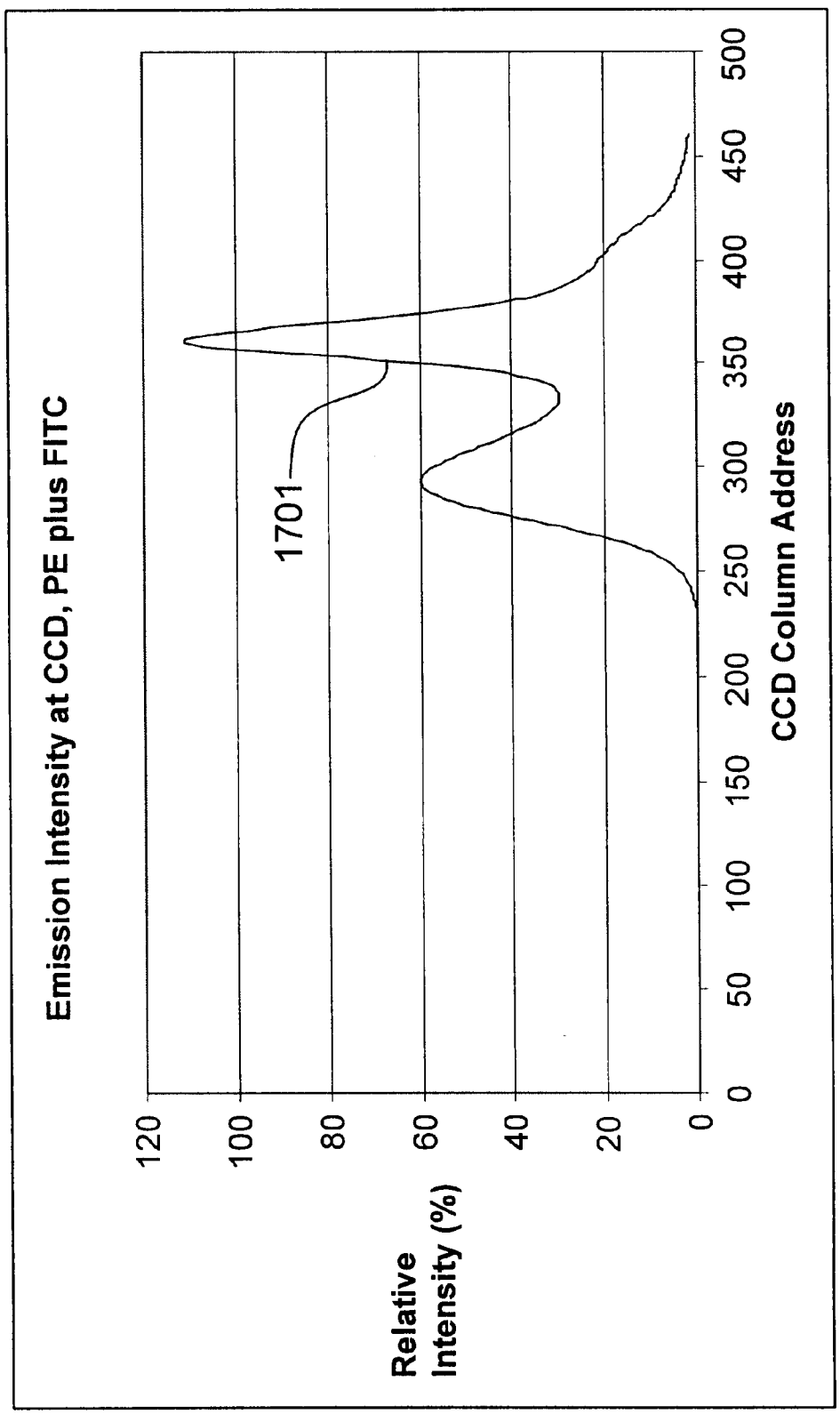
Figure 18:
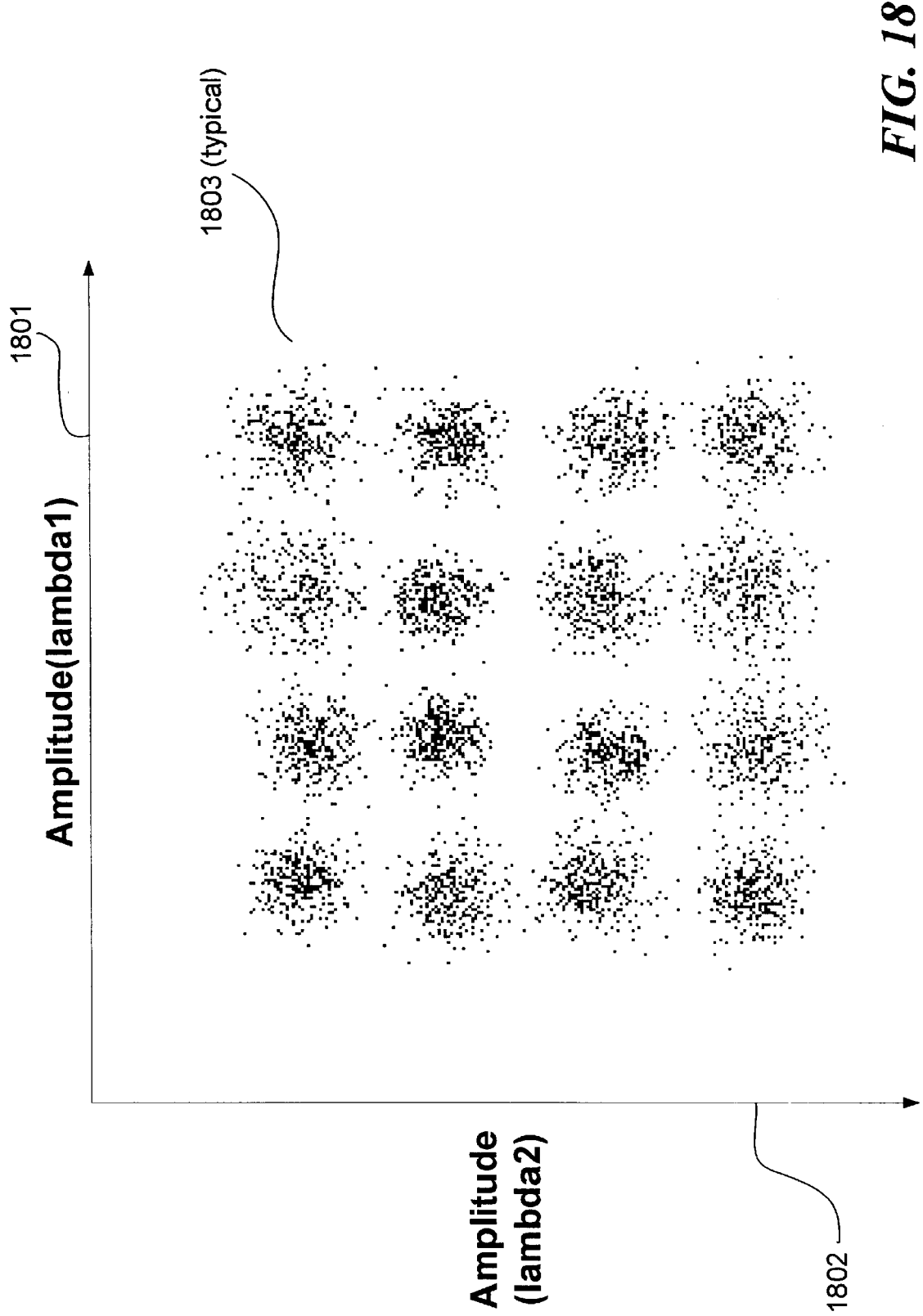
Figure 19:
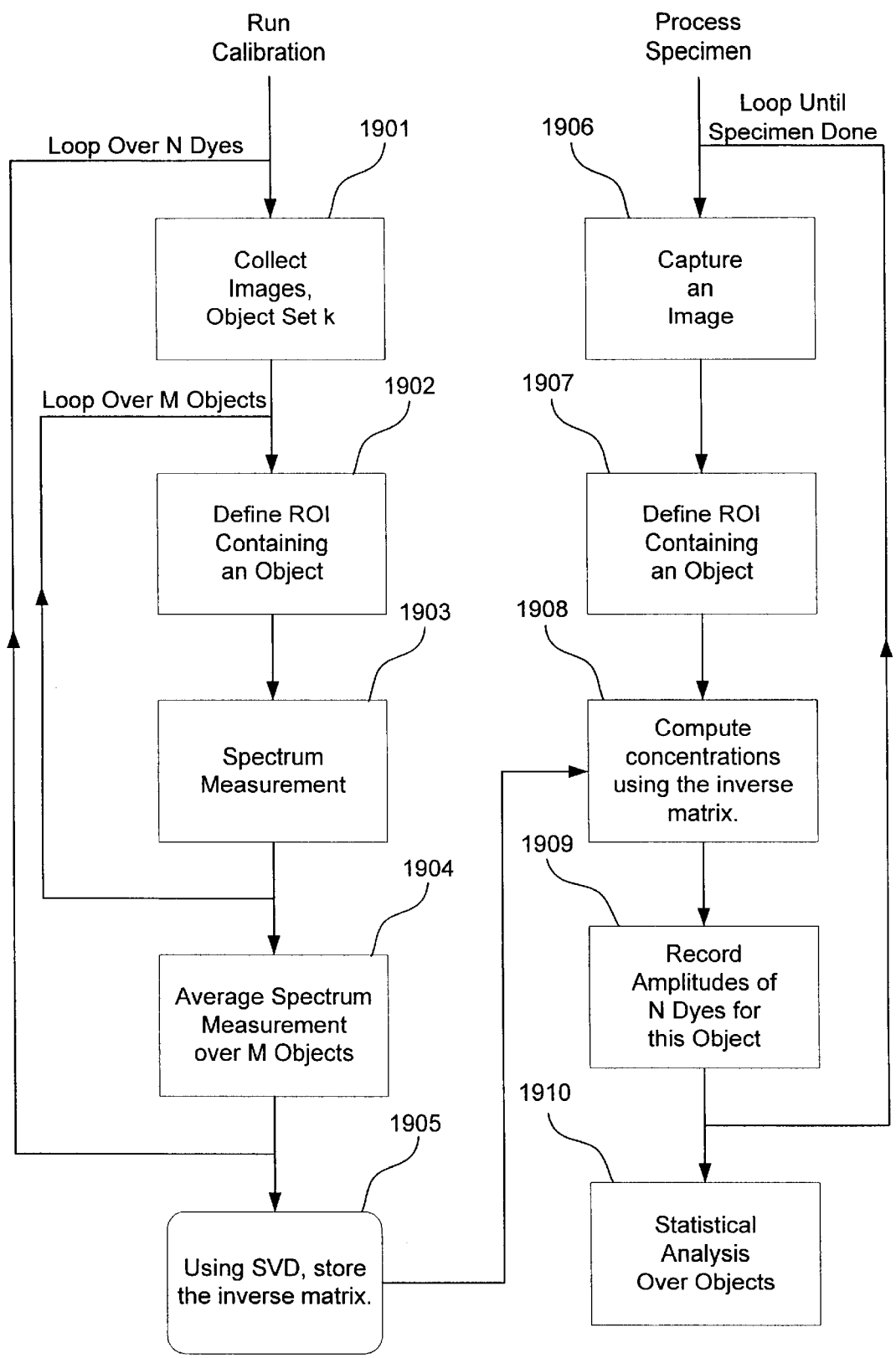

FIG. 6 schematically illustrates the encoding a microscopic bead with two fluorescent dyes;

FIG. 7 is a is a schematic diagram of a flow imaging system emphasizing a volume of specimen in the measurement cavity of the flow imaging instrument, as wells the paths of illumination, emission, and light collection;

FIG. 8 is a graphical representation of the combined emission spectra of R-Phycoerythrin and fluorescein isothiocyanate fluorophores;

FIG. 9 schematically illustrates the ray paths through a prism, establishing the definitions for the angles used in the angular deviation equation utilized in accord with the present invention;

FIG. 10 is a graphical representation of index of refraction versus wavelength for BK7 glass;

FIG. 11 is a graphical representation of emission intensity versus wavelength for R-Phycoerythrin fluorescent dye;

FIG. 12 is a graphical representation of emission intensity versus angular deviation for R-Phycoerythrin fluorescent dye after dispersion through a prism;

FIG. 13 is a graphical representation of angular deviation versus wavelength for a 60-degree prism constructed from BK7 glass;

FIG. 14 is a graphical representation of emission intensity versus cross coupled device (CCD) column address resulting from the use of a lens for focusing the dispersed light from the prism onto the CCD array;

FIG. 15 is a graphical representation of a surface plot of the image of a particle generated by the flow imaging system in which a single fluorophore contributes to the image and spectral dispersion is applied in the horizontal direction;

FIG. 16 is a flow chart of the calibration, image acquisition, and amplitude extraction operations of the present invention;

FIG. 17 is a graphical representation of emission intensity versus CCD column for the combined spectra of R-Phycoerythrin and fluorescein isothiocyanate fluorophores;

FIG. 18 is a graphical representation of a bivariate scatterplot of particles with the amplitude of the FITC signal plotted on the horizontal axis and the amplitude of the R-Phycoerythrin signal plotted on the vertical axis; and FIG. 19 is a flow chart of the calibration, image acquisition, and amplitude extraction operations using linear algebraic techniques in accord with an embodiment of the present invention.

DESCRIPTION OF THE PREFERRED EMBODIMENT

Figure 1:
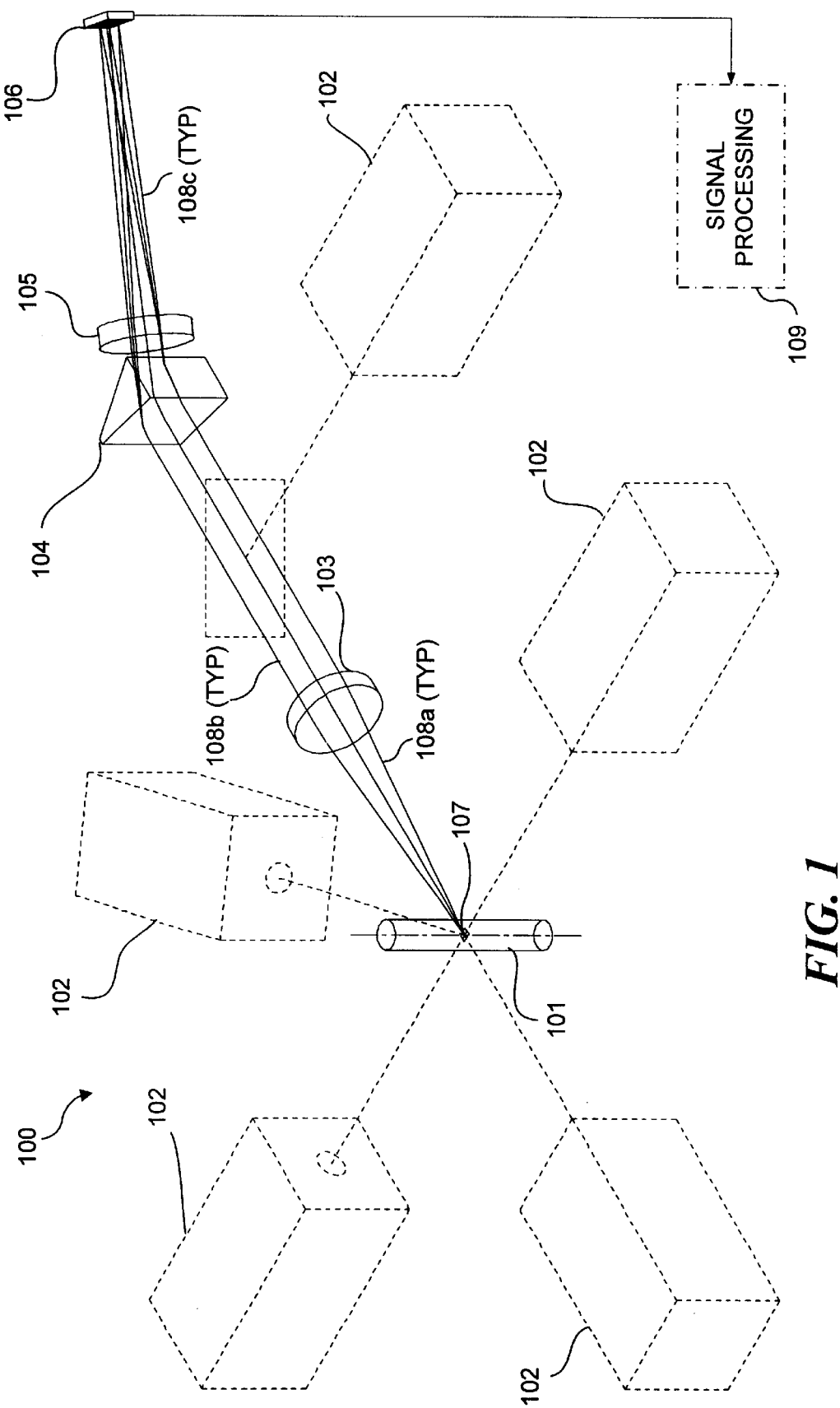
FIG. 1 is a schematic diagram of a flow imaging system using spectral dispersion in the light path between the specimen and a time delay integration camera.

FIG. 1 schematically illustrates a flow imaging system 100 using spectral dispersion and time delay integration camera technology. Particles such as biological cells suspended in a flowing liquid pass through a measurement cavity 101, where they are illuminated by one or more light sources 102. Light from particles passing through a field of view 107 travels along a ray path 108a and is collected by a first lens 103 and travels in a collimated beam along a ray path 108b through a prism 104, which maintains ray paths 108c in the vertical dimension, while also dispersing ray paths 108c in the horizontal dimension according to wavelength. An optical grating may be used in place of the prism to accomplish spectral dispersion, but care must be taken in the design of such a grating to reduce the impact of sidelobes in the dispersion function. A second lens 105 focuses the light passed by the prism onto a two-dimensional photodetector array 106 to create an image of the flowing particles.

The signals from two-dimensional photodetector array 106 are preferably processed by a signal processing means 109. However, such signals can be sent to a storage device for later processing, or sent to a separate processing device. Signal processing means 109 manipulates the signal data to analyze the image for each object passing though the system. The manner in which the signals are processed is described in more detail below. Signal processing means 109 preferably comprises a programmed computing device, that includes a microprocessor and a memory in which machine instructions are stored that cause the microprocessor to appropriately process the signals. Alternatively, the signal processing means can comprise an application specific integrated circuit (ASIC) chip that employs hardwired logic for carrying out the processing functions, or a digital oscilloscope that can be configured to provide the required signal processing capability.

FIG. 2 illustrates of ray paths 108*a*–*c* through system 100 as viewed from above and shows the dispersion effect, while FIG. 3 is an illustration of ray paths 108*a*–*c* through system 100 as viewed from the side. Note that FIG. 3 clearly shows that the prism transfers light in that dimension without changing the angles of ray paths 108*c*.

Figure 4:
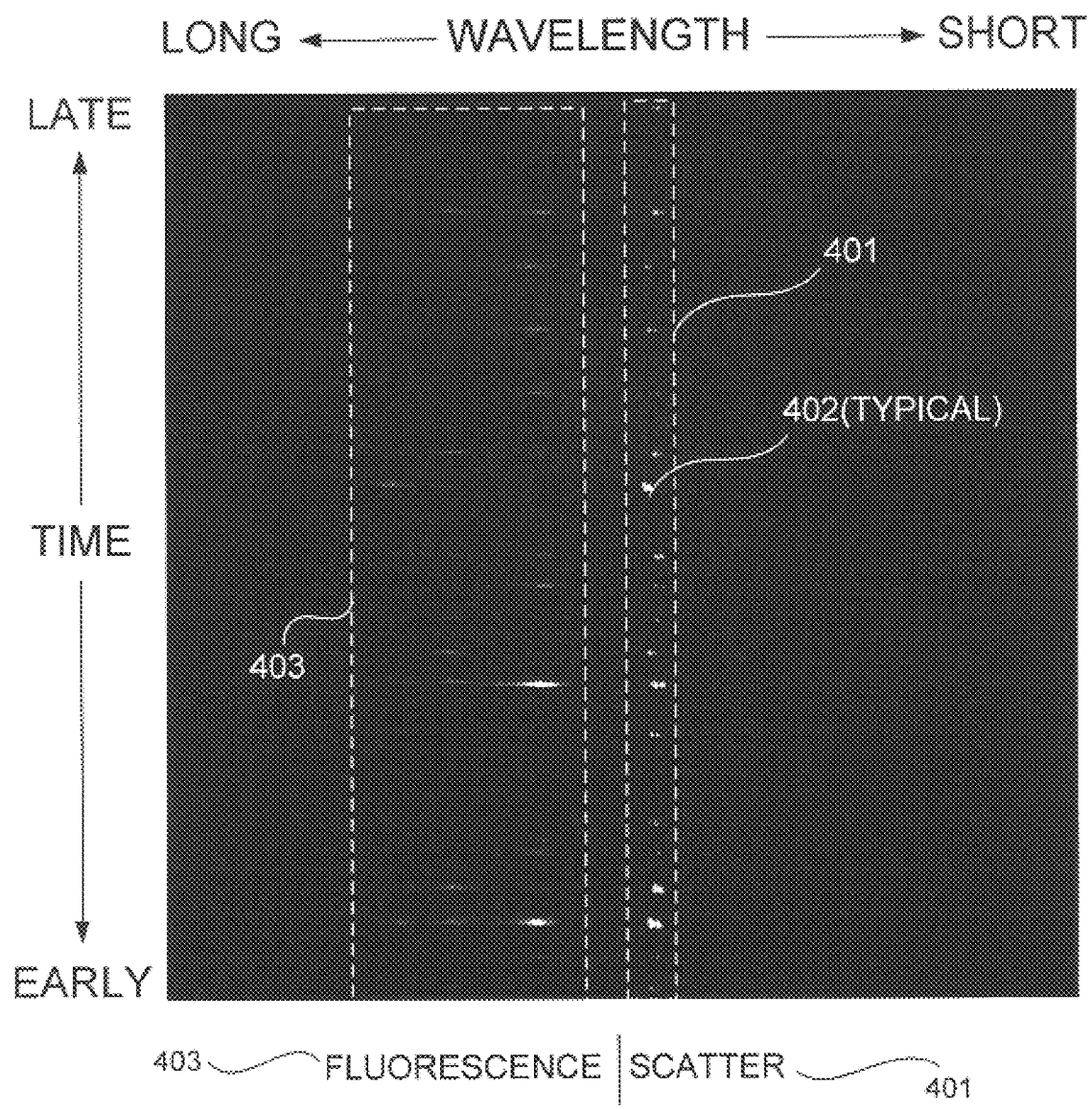
FIG. 4 is an exemplary image of biological cells captured by the flow imaging system of FIG. 1.
Figure 5:
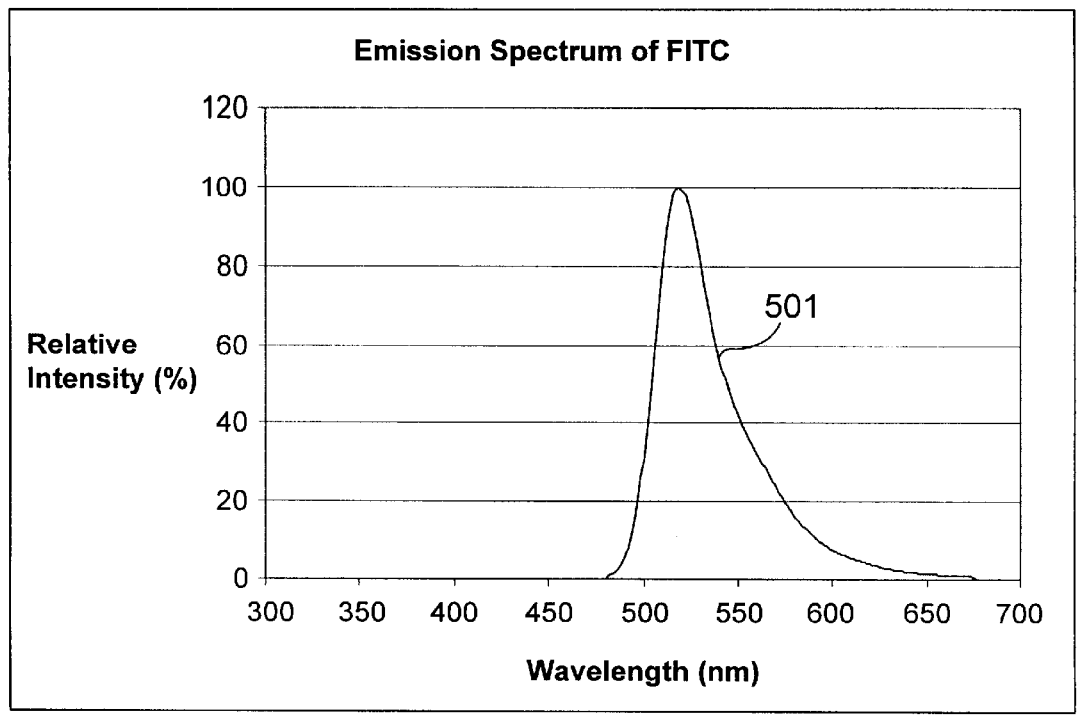
FIG. 5 is a graphical representation of the emission spectrum of fluorescein isothiocyanate, a fluorescent dye.

FIG. 4 illustrates an exemplary image that can be obtained by system 100. Although particles 402 imaged by system 100 are preferably spherical (i.e. have a circular cross-section), any spread in the spectrum of the light captured from the particles causes dispersion in the horizontal axis. In this sample image, a single coherent light source from a laser was employed to illuminate particles 402, but mechanisms of interaction of the particles with incident light contributed to this image. A first such mechanism is the scattering of light from source 102 (i.e. a laser source) into the solid collection angle defined by lens 103. The scattering mechanism does not modify the spectrum of the source, which is very well defined and compact. For this reason, the images of particles 402 seen in a column 401 in FIG. 4 depict the particles in their true round shape. A second interaction mechanism is that of fluorescence, in which light absorbed by the particles excites electrons of special dye molecules called fluorophores from their ground state to a higher energy band. The excited electrons quickly decay back to the ground state through a number of mechanisms, one of which is the emission of photons of lower energy than the excitation photons. That emission is called "fluorescence." The shift from high energy, short wavelength excitation to lower energy, longer wavelength emission is called the "Stokes shift." If a fluorescent molecule possessed only a single ground state, a single excited state, and a fixed pathway for decay, the emission spectrum would be a narrow peak similar to the excitation, but offset by the Stokes shift. However, the ground "state" and the excitation "state" are each composed of a blur of closely-spaced energy bands, and multiple energy-loss mechanisms contribute to decay. Therefore, measured fluorescence spectra are broad, and can have multiple peaks. Such a spectrum is illustrated in FIG. 5, which shows a fluorescence spectrum 501 for fluorescein isothiocyanate (FITC). The broad wavelength distributions of fluorophores translate into widening of the images generated from the light emitted by fluorescent particles, as seen in column 403 of FIG. 4.

The process of fluorescence begins with the absorption of light from the excitation source. The ability of the fluorophore molecules to absorb light is expressed as the absorption cross section, δ, related to the fractional change in intensity by the following equation:

$$\ln \frac{I_0}{I} = \sigma n d$$

where:
σ=absorption cross section (cm²/molecule)
n=concentration (molecules/cm³)
d=sample thickness (cm).

Molecular concentration, n, is related to the molar concentration, c, as follows:

$$c \frac{\text{moles}}{\text{liter}} = n \frac{\text{molecules}}{\text{cm}^3} \cdot \frac{10^3}{A} \frac{\text{cm}^3/\text{liter}}{\text{molecules/mole}}$$

where:

$$A = \text{Avagadro's number} = 6.022 \cdot 10^{23} \frac{\text{molecules}}{\text{mole}}$$

The conversion of excitation light to emitted light is described using the concept of rate constants as follows. All of the rate constants are in units of photons/molecule/sec.

$$k_e = \frac{Q_e k_a k_f}{k_a + k_f} \frac{\text{photons}}{\text{sec} - \text{molecule}}$$

where:

$$k_a = I_0 \sigma = \text{absorption rate constant}$$

$$k_f = \frac{1}{\tau_f} = \text{emission rate constant}$$

$$Q_e = \text{quantum efficiency.}$$

FIG. 6 schematically illustrates encoding a microscopic bead 601 with two fluorescent dyes. Fluorescent dye $F_1$ 603 and $F_2$ 604 are each added in controlled amounts into a container 602, along with bead 601. Then ligand reactants 605 are added to the container. The ligand reactants act to selectively bind fluorescent dyes $F_1$ and $F_2$ onto specific portions of bead 601, yielding an encoded bead 601*a*. Encoded bead 601*a* can then be read in a flow imaging system 606.

FIG. 7 schematically illustrates a volume of a specimen 701 that includes bound fluorophores in a measurement cavity 702 of a flow imaging instrument. The power emitted by the fluorophores is related to the emission rate constant, as follows:

$$P_e = k_e E_p n V \text{ watts}$$

where:

$$E_p = \frac{hc}{\lambda_e} = \text{energy of an emitted photon in joules}$$

n=fluorophore concentration in molecules/cm³
V=volume of the sphere encosing the illuminated fluorophores (cm³)
$P_e$=total emitted power.

A lens 703 collects emitted light 705 over a solid angle 706 (i.e. angle θ)] and delivers emitted light 705 to the surface of CCD photosensor array, as described in conjunction with system 100 of FIG. 1. The intensity of the emitted light reaching the CCD array is predicted as follows:

$$P_c = P_e \frac{1-\cos(\theta)}{2}$$

$$I_s = \frac{TP_c}{A_s} \frac{\text{watts}}{\text{cm}^2}$$

where:
  $P_c$=power collected by the lens
  T=transmission efficiency of the optical system
  $A_s$=area of the photosensor illuminated by emitted photons
  $I_s$=average intensity at the surface of the photosensor.

Assuming that an intensity of an excitation light 704 is not significantly attenuated as it passes through the sample volume, because of a low concentration of absorbers, each fluorophore can be treated independently by its own set of rate equations. The intensity delivered to the camera by the fluorophores of a given type is directly proportional to the concentration of that fluorophore in the imaged volume. Intensities add linearly, and the CCD photodetector translates intensity to voltage linearly. Therefore, accurate measurement of the intensities of light captured from each fluorophore species yields accurate estimates of the concentration of that species. Preservation of the linearity of translation of light intensity to image level over the full dynamic range of the CCD signal is essential. While flow cytometers may typically compress the photosensor signal by application of a logarithmic amplifier, introduction of such nonlinearity into the image capture system of the flow imaging system of the present invention is preferably avoided.

Complicating the problem of intensity measurement is the fact that the emission spectra of multiple fluorophores used in an assay can overlap, as shown in FIG. 8. Note that portions of an emission spectrum 801 for FITC and an emission spectrum 802 for R-Phycoerythrin (PE) overlap. To accurately process image data from a cell or object that includes multiple fluorophores with overlapping spectra an accurate method for the separation of the individual spectrums for each of the fluorophores is required.

The power emitted by a fluorophore is spread over a broad spectrum. The total emitted power can be computed from the spectrum using the concept of power spectral density, as follows:

$$P_e = \int_{-\infty}^{\infty} S(\lambda) d\lambda$$

where:
  $P_e$=total emitted power
  S=power spectral density

The light field captured by the camera, however, is dispersed by the prism as a function of the wavelength-dependent index of refraction, $n(\lambda)$:

$$\delta(\lambda)=\theta_{i1}+\sin^{-1}[(\sin \alpha)(n(\lambda)^2-\sin^2\theta_{i1})^{1/2}-\sin \theta_{i1} \cos \alpha]-\alpha$$

where:
  $\theta_{i1}$=angle of incidence wrt normal of first surface of prism
  $\alpha$=apex angle of the prism
  $n(\lambda)$=index of refraction of the prism material
  $\lambda$=wavelength
  $\delta$=deflection angle The angular coordinate system used in the equation above is graphically illustrated in FIG. 9. A prism 901 is modeled as an equilateral triangle with an apex angle 902 (i.e. angle $\alpha$). The magnitude of a deflection angle 904 (i.e. angle $\delta$) thus depends on the magnitude of apex angle 902, the magnitude of an angle of incidence 903 (i.e. angle $\theta_{i1}$), and the wavelength-dependent index of refraction, $n(\lambda)$.

The index of refraction is described by the following equation. The coefficients, $A_0$ through $A_5$, have been measured very precisely for common types of glass useful for building prisms. Thus for any prism employed in system 100 of FIG. 1, accurate data regarding the prism parameters is likely to be readily available:

$$n^2=A_0+A_1\lambda^2+A_2\lambda^{-2}+A_3\lambda^{-4}+A_4\lambda^{-6}+A_5\lambda^{-8}$$

FIG. 10 graphically illustrates a plot 1001 representing the index of refraction versus wavelength for BK7 glass. FIG. 11 graphically illustrates an emission spectrum 1101 for the fluorescent dye PE (the same emission spectrum is shown in FIG. 8, overlapping with the emission spectrum for FITC). FIG. 12 graphically illustrates an angular spectrum 1201 representing the emission spectrum for the fluorescent dye PE versus the angular deviation, $\delta$, produced by the prism described above.

In order to create an image such as that shown in FIG. 4 using system 100 of FIG. 1, light leaving prism 104 must be focused onto two-dimensional photodetector array 106 (i.e. a CCD array) by second lens 105. Angular spectrum 1201 of FIG. 12 is then mathematically transformed to achieve a spectrum 1301 corresponding to angular deviation verses wavelength, as shown in FIG. 13. Spectrum 1301 can then be manipulated to achieve an emission profile 1401 corresponding to the emission intensity versus the CCD column address, as shown in FIG. 14. A width 1402 of emission profile 1401 is determined by the focal length, f, of second lens 105 (of system 100 as shown in FIG. 1). The following equation relates a change in field angle, $\phi$, to a deflection along a row of the CCD array:

$$\Delta x=\tan (\Delta\phi)\cdot f \approx \Delta\phi\cdot f \tag{1}$$

where:
  f=focal length of lens
  x=position on the array
  $\phi$=field angle

For the example of FIG. 14, second lens 105 has a focal length of 100 mm, and two-dimensional photodetector array 106 (i.e. the CCD array) has a pixel pitch of 13 microns. Prism 104 (from system 100 of FIG. 1) and prism 901 (FIG. 9) are assumed to be identical, and are modeled as using BK7 glass, with apex angle 902 being 60 degrees, and angle of incidence 903 being 48 degrees. A surface plot 1501 of an image of a particle generated using such parameters is graphically illustrated in FIG. 15.

Each fluorophore used in an assay will have a characteristic image for a given particle size and shape. The particle shape is preserved in the vertical dimension of the image. However, the shape is spread by the dispersion process in the horizontal dimension. For large particles, it is necessary to deconvolve the particle shape from the image in the horizontal direction in order to restore the characteristic emission spectrum for analysis. This deconvolution operation is beyond the scope of the present invention. However, if the particle dimensions are small relative to the lateral extent of the spectral dispersion, the influence of particle width (and the deconvolution operation) can be ignored.

The goal of the image analysis is to determine the average intensity of each fluorophore for each particle in the image. A curve fitting method is used to accomplish this. The preferred form of the equations for emission spectra is the Lorentzian, as follows:

$$D(x, y) = A^2 e^{-b^2(x-x_0)^2} e^{-c^2(y-y_0)^2} \cdot \left[ w_1 + w_2 \cdot \frac{1+c_1^2 x_1^2}{1+c_1^2(x-x_1-x_0)^2} + w_3 \cdot \frac{1+c_2^2 x_2^2}{1+c_2^2(x-x_2-x_0)^2} \right]$$

where:

$w_1 = (1+\cos\theta_1)/2$
$w_2 = (1-\cos\theta_1)(1+\cos\theta_2)/4$
$w_3 = (1-\cos\theta_1)(1-\cos\theta_2)/4$ The equation describes a surface that is fundamentally Gaussian shaped in both the x and the y directions, with the Gaussian decay rate set by parameters "b" and "c." It accommodates up to three peaks in the x direction, at "$x_0$," "$x_1$," and "$x_2$," and a vertical position of "$y_0$." The angles "$\theta_1$" and "$\theta_2$" and the constants "$c_1$" and "$c_2$" set the relative weights of the three terms. The amplitude, "A," is the solution that is sought by way of fitting the expression on the right of the equal sign to the measured data, D(x,y).

In all, eleven independent variables comprise the analytical expression for the spectrum. Furthermore, this equation describes only one fluorophore. The general expression for a collection of N fluorophores is as follows:

$$D(x, y) = \sum_{k=1}^{N} A_k e^{-b_k^2(x-x_{0k})^2} e^{-c_k^2(y-y_0)^2} [w_{1,k} + w_{2,k} B_k + w_{3,k} C_k]$$

where:

$$B_k = \frac{1 + c_{1,k}^2 x_{1,k}^2}{1 + c_{1,k}^2(x - x_{1,k} - x_{0,k})^2}$$

$$C_k = \frac{1 + c_{2,k}^2 x_{2k}^2}{1 + c_{2,k}^2(x - x_{2,k} - x_{0,k})^2}$$

The number of parameters to be accommodated in the optimization grows linearly with the number of fluorophores. Iterative approximation routines are available for finding the values of multiple parameters in an expression. Typically, such algorithms compute the derivative of the error between the expression and the data with respect to each parameter, and adjust the parameters iteratively until some maximum error criterion is satisfied. The stability of such methods is highly dependent on employing expressions that do not allow singularities and that are differentiable. Furthermore, convergence is usually to a local minimum in the region of a useful set of initial parameter values. All of these conditions can be met using the Lorentzian form, but computation time may be very long for cases of multiple fluorophores.

The nonlinear conjugate gradient method of optimization is used in the preferred embodiment. In this method, an expression for, or model of, the data is developed that approximates the data set. The expression is modified through an iterative process that minimizes the error between the data and the values generated using the expression. In the method of the present invention, the model of the data is the Lorentzian expression for multiple fluorophores, which carries a large number of free parameters that must be optimized. For each step in the optimization, a parameter is modified, the error between the data and the model computed, and the gradient of the error with respect to the parameter is calculated. The model is modified to push the error in a direction orthogonal to the gradient, i.e., in the direction that appears best for reducing the error.

The nonlinear conjugate gradient method minimizes an error function f(x) that is defined. A reasonable error function might be the mean square error between the data and the model. The steps in the nonlinear conjugate gradient method are as follows. Note that lower case letters denote vectors, upper case letters denote matrices, and upper case Greek letters denote scalars:

$$d_{(0)} = r_{(0)} = -f'(x_{(0)})$$

where:

$d_{(0)}$ = initial value of the direction vector
$r_{(0)}$ = initial value of the residual
$x_{(0)}$ = initial set of arguments for the error function
f'(x) = gradient of the error function After initializing the direction vector, the algorithm moves toward convergence by updating the direction vector, $d_{(i)}$, the residual, $r_{(i)}$, and the arguments to the error function, $x_{(i)}$. The first step in each iteration is to transform the direction vector by multiplying by vector $\alpha_{(i)}$, which is generated by meeting the orthogonality condition:

$$x^T y = \sum_{i=1}^{n} x_i y_i = 0$$

specifically, find $\alpha_{(i)}$ such that:

$$[f'(x_{(i)} + \alpha_{(i)} d_{(i)})]^T d_{(i)} = 0$$

Next, a new set of arguments is generated by adjustment in a direction orthogonal to the direction vector:

$$x_{(i+1)} = x_{(i)} + \alpha_{(i)} d_{(i)}$$

If $f(x_{(i+1)})$ is still too large, another iteration is started, beginning with the adjustment of the direction vector:

$$d_{(i+1)} = r_{(i+1)} + \beta_{(i+1)} d_{(i)}$$

where:

$$\beta_{(i+1)} = \frac{\|r_{(i+1)}\|}{\|r_{(i)}\|} = \frac{r_{(i+1)}^T r_{(i+1)}}{r_{(i)}^T r_{(i)}}$$

and:

$$r_{(i+1)} = -f'(x_{(i+1)})$$

Fundamental to the convergence of the nonlinear conjugate gradient algorithm is that the error function must be differentiable. Convergence to a local minimum, rather than a global minimum, suffices to solve the problem. Even under these conditions, computation time may be excessive if a large number of free parameters contribute to the error function.

A very significant improvement is accomplished by first establishing the values of the parameters for each fluorophore that depend only on the characteristics of the fluorophore, not the concentration of the fluorophore or the location of the particle in the image. This can be accomplished by collecting images of beads labeled with a single fluorophore and running the optimization algorithm on a number of particles in the images. Once this has been accomplished for all fluorophores in an assay and the fixed parameters stored in tables, the system is ready to run assays with multiple fluorophores present in the specimen.

When collecting and analyzing images from specimens stained with multiple fluorophores, only the amplitudes, "$A_k$," and the positions "$x_{0,k}$" and "$y_{0,k}$" need be optimized. The other positions, "$x_{1,k}$" and "$x_{2,k}$" are known by their fixed offsets from "$x_{0,k}$." Furthermore, reasonable starting points for "$x_{0,k}$" and "$y_{0,k}$" can be found from the position of the particle in its scattering image, since the fluorescent images will reside at known offsets relative to the scattering image. Using this method, the number of free parameters in the optimization is greatly reduced, and the positional parameters are given starting points close to their values for minimum fit error. FIG. 16 is a flow chart of the sequence of logical steps in a preferred calibration and runtime optimization process.

To accomplish calibration, images of singularly-stained beads are collected in a block 1601, for a large number, M, of beads. The image of each bead is cropped into a region of interest in a block 1602. The optimization algorithm is applied to the region of interest to yield estimates of the parameters "$b_k$," "$c_k$," "$\theta_{1,k}$," "$\theta_{2,k}$," "$c_{1,k}$," and "$c_{2,k}$" for a bead in a block 1603. The offsets, $(x_{1,k}-x_{0,k})$ and $(x_{2,k}-x_{0,k})$ between the first peak and the other two peaks, if present in the emission spectrum, are also determined during calibration. The parameter estimates are averaged over M beads to improve the accuracy of the parameter estimates in a block 1604. The calibration is repeated for each of N dyes, and the parameter estimates are stored in a table in a block 1605. The parameters delivered by calibration will be valid as long as the flow imaging instrument characteristics remain stable and the dyes used in calibration continue to be used to stain the specimens.

After the system is calibrated, processing of actual samples can begin. During the processing of a specimen, images are captured in a block 1606, and cropped into region-of-interest sub-images in a block 1607. The optimization algorithm is applied to each sub-image in a block 1608, using the expression encompassing all N dyes in the mixture used to stain the specimen. The parameters delivered by calibration remain fixed while the amplitudes, "$A_k$" and the positions "$x_{0,k}$" and "$y_{0,k}$" are optimized. The amplitudes for each of the N dyes on each object are recorded in a block 1609, and a statistical analysis of each object is performed in a block 1610. As discussed above, a useful statistical analysis is to separate the spectrums of each dye associated with an object, so that quantities of each individual dye can be determined. For cells, different structures are identified with different dyes, thus the quantity of a specific dye associated with a cell corresponds to a quantitative determination of structures associated with that cell.

A key step in the optimization process is that of generating a robust data set D(x,y) for each particle in the image record. This process is comprised of the steps of detecting the arrival of the particle in the image record and selection of the pixels to be included in a region of interest over which the curve fitting is to be performed. Preferred methods for detecting particles and generating the region-of-interest definitions are disclosed in a commonly assigned Provisional Patent Application No. 60/306,126 entitled "COMPUTATIONAL METHODS FOR THE SEGEMENTATION OF IMAGES OF OBJECTS FROM BACKGROUND IN A FLOW IMAGING INSTRUMENT".

The use of a calibration process applied to each one of the dyes individually offers the additional advantage of including the characteristics of the imaging system in the descriptions of the characteristic spectra. An alternative approach would be to begin with spectra provided by the dye manufacturers, and to predict the particle images from measurements of the system performance.

FIG. 17 is a graphical representation of the combined spectra 1701 generated by an image of an object dyed with roughly equal intensities of the fluorescent dyes PE and FITC. Tables 1 and 2 show the values of the parameters that produce an approximate fit to this spectrum.

Accomplishing the optimal fitting of the Lorentzian description of a spectrum generated by a combination of fluorophores yields an amplitude value for each of the fluorophores used in the assay for each detected particle. If every particle were imaged with a very high signal-to-noise ratio, and fluorophore characteristics were robust against any chemical, optical, or electronic sources of error, the set of amplitudes would serve to completely classify the particle. In many practical situations, however, low signal-to-noise ratio and the presence of perturbations to the fluorophore spectra will cause spreading in the spectral shapes.

TABLE 1

Optimized Parameters for PE

| | |
|---|---|
| A | 5.9 |
| B | 0.02 |
| $c_1$ | 0.11 |
| $c_2$ | 0.08 |
| $x_0$ | 395 |
| $x_1$ | −35 |
| $x_2$ | 15 |
| $\theta_1$ | 1.07 |
| $\theta_1$ | 0.7 |
| $y_0$ | 64 |
| C | 0.01 |

TABLE 2

Optimized Parameters for FITC

| | |
|---|---|
| A | 7.0 |
| B | 0.025 |
| $c_1$ | 0.05 |
| $c_2$ | 0.06 |
| $x_0$ | 300 |
| $x_1$ | −22 |
| $x_2$ | 60 |
| $\theta_1$ | 1.3 |
| $\theta_1$ | 0.7 |
| $y_0$ | 64 |
| C | 0.01 |

An analysis method useful for accommodating spreading in the spectral shapes is that of cluster analysis applied to scatter plots. FIG. 18 is a graphical representation of a hypothetical bivariate scatterplot of particles imaged and analyzed on a flow imaging system using the methods of the present invention. A horizontal axis 1801 represents the intensity of light from a first fluorophore encoding marker beads, and a vertical axis 1802 represents the intensity of light from a second fluorophore encoding the same marker beads. A particular version of the marker bead is characterized by the concentrations of the two fluorophores diffused into the bead. In the example of FIG. 18, a total of 16 bead versions are present in the scatterplot, since four concentrations of each of two fluorophores are used to encode the beads. Each version produces a cluster 1803 of points on the plane defined by the amplitudes $A(\lambda_1)$ and $A(\lambda_2)$. Established methods of cluster analysis or principal component analysis are available for identifying the particles belonging to each of the sixteen versions. Using such methods accommodates some uncertainty in the production of the beads and in capturing and analyzing bead images. Control over these variables is necessary only to the degree necessary to stay within the dynamic range of the imaging system and to provide reasonable separation of the clusters in the scatter plots.

An astute reader may recognize that the emission spectra for a set of fluorophores form a set of linear algebra basis vectors. Hence linear algebra techniques can be utilized to determine a particle's concentration of fluorophores. Thus one embodiment of the present invention utilizes such linear algebra techniques to determine a particle's concentration of fluorophores. A brief introduction of this algebraic technique will be provided, followed by a formal presentation of the algebra required. To simplify the presentation, it is assumed that the measured emission spectrum of a particle is known. The details of measuring the emission spectrum will follow the presentation of the algebra. The steps of calibration and specimen processing remain identical to the processing described above.

FIG. 5 is a graphical representation of the emission spectrum of the fluorescent dye FITC. FIG. 8 is a graphical representation of the overlay of two unique emission spectra, for PE and FITC fluorophores. If a particle contains PE and FITC fluorophores, then the emission spectrum would be an additive combination of the two plots in FIG. 8. Note that because most specimens do not naturally include fluorophores (i.e. such fluorophores are added), control over the specific fluorophores added can be achieved, thus a combined spectrum similar to that illustrated in FIG. 8 can be determined for each potential fluorophore that may be present on a specimen. Each individual emission spectrum for a potential fluorophore, and the combined spectrum for all potential fluorophores, each can be regarded as functions, or characteristic images, that form a basis in a vector space. Other functions that form a basis in a two dimensional vector space are sine and cosine in quadrature modulation/demodulation communication transmissions whose two dimensional signal patterns can be identical to the scatter plot of FIG. 18. Referring to the emission spectrum for a particle containing PE and FITC fluorophores (FIG. 8), the spectrum can be represented as a linear combination of the two fluorophore functions (i.e. individual spectrum of PE, shown in FIG. 11 and FITC, shown in FIG. 5). Hence, linear algebra techniques are used to decompose the emission spectra into its basis functions.

Given that the emission spectra are not identical, the squared error $$\varepsilon = \int \left( e(\lambda) - \sum_i c_i f_i(\lambda) \right)^2 d\lambda \quad (2)$$

is to be minimized where $e(\lambda)$ is the measured emission spectrum and $f_i(\lambda)$ and $c_i$ are the respective fluorophore functions and concentrations. To minimize Equation (2) with respect to concentration, take partial derivatives with respect to $c_i$. The result is a set of linear equations such that there is a matrix A that satisfies $$c = Am \quad (3)$$

where vector c represents the actual concentrations of the particle's fluorophores, and vector m is defined by:

$$m_i = \int f_i(\lambda) m(\lambda) d\lambda \quad (4)$$

where $m(\lambda)$ is the measured spectrum. Therefore, to minimize Equation (2), the concentration coefficients are determined by a matrix A, which is the inverse of matrix F. Matrix F's row and column elements are defined by $$F_{ij} = \int f_i(\lambda) f_j(\lambda) d\lambda \quad (5)$$

The preferred technique for computing a particle's concentration of fluorophores is now presented. The emission spectra discussed are represented as a continuous waveform.

FIG. 17 depicts the instrument's representation of the emission spectra of a particle containing two fluorophores, so the emission spectra are represented digitally as a vector where the x-axis are the columns of the CCD detector. The value of each element of the vector is the y-axis. Instead of a continuous waveform, the emission spectrum represented by the instrument is a sampled version of the continuous waveform. The sampled version is also considered as a vector with finite dimension. Let S be a matrix whose columns represent the sampled emission spectrum of each fluorophore. S has columns equal to the number of possible fluorophores (N columns) and rows equal to the number of pixels (n rows) orthogonal to the time axis with respect to the CCD detector.

Analogous to Equation (2), the following measure of error is to be minimized:

$$\epsilon = (m - Sc)^T (m - Sc) \quad (6)$$

where m is the vector, n long, representing the measured spectrum and c is a vector N long representing the concentrations. To minimize Equation (6) with respect to the concentrations, take partial derivatives with respect to concentrations $c_i$ and solve for zero partial derivatives. The following equations show some intermediate steps of the minimization that simplify and yield the final solution:

$$S^T(Sc - m) = 0$$

$$S^T S c - S^T m = 0$$

$$c = (S^T S)^{-1} S^T m \quad (7)$$

$$c = S^{-1} (S^T)^{-1} S^T m$$

$$c = S^{-1} m$$

Since S is not a square matrix, singular value decomposition is used to invert S.

Given the matrix S. There exists a singular value decomposition with matrices U, V and W such that:

V is a square matrix with dimension equal to the columns of S.

U is a matrix with dimension equal to S.

$V^T V = U^T U = 1$ where 1 is the identity square matrix of dimension V.

W is a diagonal matrix with dimension equal to the columns of S.

$S = UWV^T$.

Therefore, to minimize Equation (6), the concentrations are determined by $$c = VW^{-1} U^T m$$

Referring once again to Equation (1) and FIG. 14, the resulting spectrum in FIG. 17 has a width dependent upon the fluorophores and the instrument components, and a beginning position dependent upon the particle's position within the flow cell (as is described above with respect to FIG. 14). The length of the spectrum can be set to fixed length in CCD pixels, which is determined by the minimum and maximum frequency content of the fluorophores. The relative pixel position is determined by Equation (1) to be a direct translation (pixel for pixel) of the particle's position on the CCD, and a reference of position can be obtained from the scatter channel shown in FIG. 4 (i.e. column 401). Note that there is also depth of the spectrum along the time axis in FIG. 4. Therefore, the spectrum should be accumulated along the time axis to obtain a measurement of fluorescent content.

To determine the emission spectrum for a particle, a pixel positional reference must be established for, the scatter and fluorescence channel on the CCD. When an object's region of interest (ROI) is determined in the scatter channel, the ROI's height and position along the time axis in FIG. 4 determine the accumulation of the spectrum along that axis. Its lateral position can be determined by the particle's centroid in the lateral position, which can be determined as a weighted average in the ROI and the weights are the intensity of the scatter. Since the spectrum captured in the fluorescence channel is a digital sample of a continuous spectrum, the lateral shift, which is determined by the centroid, can be resampled to within sub-pixel accuracy by Taylor series for functional approximation around a pixel position. Other common interpolation techniques may also be used, such as a cubic spline interpolation.

Analogous to FIG. 16, FIG. 19 is a flowchart of the calibration and specimen processing utilizing the above describe linear algebra embodiment. Some of the steps, but not all, are identical. To accomplish calibration, images of singularly-stained beads are collected for a large number, M, of beads in a block 1901. The image of each bead is cropped into a ROI in a block 1902. The spectrum measurement utilizes ROI and scatter image information to yield estimates of the position which aids in determining the spectrum for a bead in a block 1903 (note the differences in FIGS. 16 and 19; in block 1603 a 2D optimization was performed, while in block 1903 a spectrum measurement is performed as described). The spectrum estimates for each of the M beads are averaged in a block 1904, to improve the accuracy of the spectrum estimates. The calibration is repeated for each of N dyes resulting in a matrix X with N columns. The number of rows in matrix X is determined by the range of spectrum frequency responses projected onto the CCD. After the matrix X is determined, singular value decomposition (SUD) is utilized to store the inverse of matrix X in a block 1905. The inverse of matrix X delivered by the above calibration will be valid as long as the flow imaging instrument characteristics remain stable and the dyes used in calibration continue to be used to stain the specimens.

During the processing of a specimen, images are captured in a block 1906 and cropped into ROI sub-images in a block 1907. The spectrum measurement algorithm is applied to each sub-image using the expression encompassing all N dyes in the mixture used to stain the specimen, in a block 1908. The concentration of each sub-image's fluorophores are computed and recorded in a block 1909. A statistical analysis of the collected data can then be performed in a block 1910.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for determining a relative concentration of a specific fluorophore associated with an object, comprising the steps of:
   (a) focusing light from an object along a collection path, the object comprising at least two different fluorophores;
   (b) dispersing the light that is traveling along the collection path into a plurality of light beams, such that each light beam corresponds to a different wavelength;
   (c) focusing each of the light beams to produce respective images for the light beams;
   (d) providing a detector disposed to receive the respective images and in response, generating an electrical signal;
   (e) processing the electrical signal to separate the electrical signal into portions corresponding to each one of the at least two different fluorophores; and
   (f) deriving an amplitude for each portion of the electrical signal that corresponds to one of the at least two different fluorophores, the amplitude for each fluorophore corresponding to a relative concentration for that fluorophore.

2. The method of claim 1, wherein the step of processing the electrical signal comprises the step of using curve fitting to distinguish different portions of the electrical signal corresponding to different fluorophores from one another.

3. The method of claim 2, wherein the step of using curve fitting comprises the step of using Lorentzian equations.

4. The method of claim 2, further comprising the step of obtaining a model of the spectra of the at least two fluorophores before processing the electrical signal, and wherein the step of using curve fitting to distinguish different portions of the electrical signal comprises the step of using nonlinear conjugation to reduce an error between the electrical signal and the model.

5. The method of claim 4, wherein the step of using nonlinear conjugation is performed iteratively.

6. The method of claim 4, wherein the error reduced by the nonlinear conjugation comprises a mean square error between the model and the electrical signal.

7. The method of claim 4, further comprising the step of providing the spectra for each fluorophore.

8. The method of claim 4, wherein the spectra for each fluorophore is generated by:
   (a) focusing light from an object along a collection path, the object comprising a single fluorophore;
   (b) dispersing the light that is traveling along the collection path into a plurality of light beams, such that each light beam corresponds to a different wavelength;
   (c) focusing each of the light beams to produce respective images for the light beams;
   (d) providing a detector disposed to receive the respective images and in response, generating an electrical signal; and
   (e) processing the electrical signal to determine a spectrum of the single fluorophore.

9. The method of claim 1, wherein the step of processing the electrical signal comprises the step of solving a set of linear equations corresponding to an emission set defined by the fluorophores that the object comprises.

10. The method of claim 9, wherein the detector comprises a scatter channel and a fluorescence channel, and wherein the step of solving a set of linear equations comprises the steps of:
   (a) establishing a pixel positional reference for the scatter channel and the fluorescence channel of the detector; and
   (b) determining a lateral shift in the fluorescence channel.

11. The method of claim 10, wherein the step of determining a lateral shift in the fluorescence channel comprises the step of determining the lateral shift with sub-pixel accuracy.

12. The method of claim 1, further comprising the step of using cluster analysis to accommodate for spectral spreading and to refine amplitude data derived from the electrical signal.

13. An imaging system for determining a relative concentration of a specific fluorophore associated with an object, comprising:
   (a) a collection lens disposed so that light traveling from the object passes through the collection lens and travels along a collection path;
   (b) a dispersing component disposed in the collection path so as to receive the light that has passed through the collection lens, dispersing the light into a plurality of light beams, each light beam being directed away from the dispersing component in a different predetermined direction;
   (c) an imaging lens disposed to receive the light beams from the dispersing component, thereby producing an image from each different one of the light beams at a different predetermined location;
   (d) a detector disposed to receive the plurality of images produced by the imaging lens, the detector producing an output signal; and
   (e) means for processing the output signal to:
      (i) separate the output signal into portions corresponding to different fluorophores; and
      (ii) derive an amplitude for each portion of the output signal that corresponds to different fluorophores, the amplitude for each fluorophore corresponding to a relative concentration for that fluorophore.

14. The imaging system of claim 13, wherein the dispersing component comprises a prism.

15. The imaging system of claim 13, wherein the dispersing component comprises an optical grating designed to reduce sidelobe dispersion.

16. The imaging system of claim 13, wherein the detector comprises a two-dimensional array.

17. The imaging system of claim 13, wherein the detector comprises a time delay integration detector.

18. The imaging system of claim 13, wherein the detector preserves a linearity of light intensity to image level over substantially a full dynamic range of the detector.

19. The imaging system of claim 13, wherein said means for processing comprises a computing device.

20. A method for processing an electrical signal containing data from at least two sources, to separate the electrical signal into components corresponding to each of the at least two sources, comprising the steps of:
   (a) obtaining the electrical signal containing data from at least two sources;
   (b) processing the electrical signal to separate the electrical signal into portions corresponding to each of the at least two sources, said processing including at least one of:
      (i) utilizing a nonlinear conjugation, said nonlinear conjugation reducing the number of free parameters to be optimized by using data collected from an optimization calibration individually executed for each source; and
      (ii) solving a set of linear equations corresponding to a data set defined by the sources; and
   (c) deriving an amplitude for each portion of the electrical signal that corresponds to one of the at least two sources.

21. The method of claim 20, wherein each source comprises a fluorophore, and wherein the amplitude for each fluorophore corresponds to a relative concentration for that fluorophore.

22. The method of claim 20, wherein the step of utilizing a nonlinear conjugation comprises the steps of:
   (a) obtaining a model of the spectra of the at least two sources before processing the electrical signal;
   (b) using curve fitting to distinguish different portions of the electrical signal that correspond to different sources from one another, and
   (c) using said nonlinear conjugation to reduce an error between the electrical signal and the model.

23. The method of claim 22, wherein the step of using curve fitting comprises the step of using Lorentzian equations.

24. The method of claim 20, further comprising the step of using cluster analysis to accommodate spectral spreading and to refine amplitude data derived from the electrical signal.

25. The method of claim 20, wherein the step of using nonlinear conjugation is performed iteratively.

26. The method of claim 22, wherein the error that is reduced by the nonlinear conjugation comprises the mean square error between the model and the electrical signal.

27. The method of claim 22, further comprising the step of providing the spectra for each source.

28. The method of claim 22, wherein the spectra for each source is obtained by:
   (a) focusing light from an object along a collection path, the object comprising a single source;
   (b) dispersing the light that is traveling along the collection path into a plurality of light beams, such that each light beam corresponds to a different wavelength;
   (c) focusing each of the light beams to produce respective images for the light beams;
   (d) providing a detector disposed to receive the respective images and in response, generating an electrical signal; and
   (e) processing the electrical signal to determine a spectrum of the single source.

29. The method of claim 28, wherein the step of providing a detector comprises the step of providing a detector that preserves a linearity of light intensity to image level over substantially a full dynamic range of the detector.

30. A method for processing an electrical signal containing data from at least two sources, to separate the electrical signal into components corresponding to each of the at least two sources, comprising the steps of:
   (a) obtaining the electrical signal containing data from at least two sources;
   (b) converting the electrical signal into a two-dimensional digital representation;
   (c) identifying portions of the two-dimensional digital representation that correspond to each of the at least two sources; and (d) performing a digital optimization to derive an amplitude for each portion of the two-dimensional digital representation that corresponds to one of the at least two sources, by fitting the two-dimensional digital representation to a parameterized model based on known data corresponding to each of the at least two sources.

31. The method of claim 30, further comprising the step of using cluster analysis to accommodate spectral spreading and to refine amplitude data derived from the electrical signal.

32. The method of claim 30, wherein each source comprises a fluorescent dye, and wherein the known data corresponding to each of the at least two sources comprise a spectrum corresponding to a specific fluorescent dye.

33. The method of claim 30, further comprising the step of providing the spectrum corresponding to each fluorescent dye before obtaining the electrical signal.

34. The method of claim 30, further comprising the step of collecting the spectrum for each fluorescent dye before obtaining the electrical signal.

35. The method of claim 30, wherein the step of fitting comprises the step of utilizing a conjugate gradient optimization.

36. The method of claim 30, wherein the step of performing the digital optimization comprises the step of deriving the amplitudes by satisfying a set of linear equations.

37. The method of claim 30, wherein the step of obtaining the electrical signal comprising the steps of:
   (a) focusing light from an object along a collection path, the object comprising at least two different fluorescent sources that emit light;
   (b) dispersing the light that is traveling along the collection path into a plurality of light beams, such that each light beam corresponds to a different wavelength;
   (c) focusing each of the light beams to produce respective images for the light beams; and
   (d) providing a detector disposed to receive the respective images and in response, generating the electrical signal.

38. The method of claim 37, further comprising the step of deconvolving a shape of the object from the images.

39. The method of claim 37, wherein the step of providing a detector comprises the step of providing a detector that preserves a linearity of light intensity to image level over substantially a full dynamic range of the detector.

* * * * *